US010376394B2

(12) United States Patent
Kaufmann et al.

(10) Patent No.: US 10,376,394 B2
(45) Date of Patent: Aug. 13, 2019

(54) SCAFFOLD SYSTEM FOR TISSUE REPAIR

(71) Applicant: BOARD OF REGENTS, THE UNIVERSITY OF TEXAS SYSTEM, Austin, TX (US)

(72) Inventors: J. Jordan Massey Kaufmann, San Antonio, TX (US); C. Mauli Agrawal, San Antonio, TX (US); Steven R. Bailey, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/854,314

(22) Filed: Dec. 26, 2017

(65) Prior Publication Data

US 2018/0200084 A1 Jul. 19, 2018

Related U.S. Application Data

(63) Continuation of application No. 15/043,968, filed on Feb. 15, 2016, now Pat. No. 9,849,007, which is a
(Continued)

(51) Int. Cl.
*A61F 2/82* (2013.01)
*A61L 27/56* (2006.01)
(Continued)

(52) U.S. Cl.
CPC .................. *A61F 2/82* (2013.01); *A61F 2/07* (2013.01); *A61L 27/18* (2013.01); *A61L 27/227* (2013.01);
(Continued)

(58) Field of Classification Search
CPC .......... A61F 2/82; A61F 2002/82; A61F 2/01; A61F 2/06; A61F 2/954; A61F 2/962;
(Continued)

(56) References Cited

U.S. PATENT DOCUMENTS

| 4,329,743 A | 5/1982 | Alexander et al. .................. 3/1 |
| 9,259,334 B2 * | 2/2016 | Kaufmann ............. A61L 27/56 |

(Continued)

FOREIGN PATENT DOCUMENTS

| JP | 2008-532643 | 8/2008 | ............. A61B 19/00 |
| WO | WO 08/154608 | 12/2008 | ............... A61F 2/82 |
| WO | WO 11/113001 | 9/2011 | ............... A61F 2/06 |

OTHER PUBLICATIONS

Diehm, N., et al. "Novel Insight Into the Pathobiology of Abdominal Aortic Aneurysm and Potential Future Treatment Concepts" Progress in Cardiovascular Disease, 2007. 50(3): p. 209-217.
(Continued)

*Primary Examiner* — Alvin J Stewart
(74) *Attorney, Agent, or Firm* — David G. Rosenbaum; Benjamin D. Rotman; Rosenbaum IP, P.C.

(57) ABSTRACT

A device for treating a damaged tissue includes an expandable scaffold positionable in a portion of a luminal tissue structure of a mammal; and maintained via stent technology, wherein the scaffold is comprised of electrospun fibers composed of a biodegradable compound. The scaffold serves as a temporary template that allows the tissue to be rebuilt.

9 Claims, 24 Drawing Sheets

Related U.S. Application Data continuation of application No. 13/766,530, filed on Feb. 13, 2013, now Pat. No. 9,259,334.

(60) Provisional application No. 61/598,125, filed on Feb. 13, 2012.

(51) Int. Cl.
| | |
|---|---|
| *A61F 2/07* | (2013.01) |
| *D04H 1/4391* | (2012.01) |
| *D04H 1/728* | (2012.01) |
| *A61L 27/50* | (2006.01) |
| *A61L 27/58* | (2006.01) |
| *A61L 27/34* | (2006.01) |
| *A61L 31/10* | (2006.01) |
| *A61L 31/14* | (2006.01) |
| *A61L 27/18* | (2006.01) |
| *A61L 27/22* | (2006.01) |
| *A61L 27/54* | (2006.01) |

(52) U.S. Cl.
CPC .............. *A61L 27/34* (2013.01); *A61L 27/50* (2013.01); *A61L 27/507* (2013.01); *A61L 27/54* (2013.01); *A61L 27/56* (2013.01); *A61L 27/58* (2013.01); *A61L 31/10* (2013.01); *A61L 31/14* (2013.01); *A61L 31/146* (2013.01); *A61L 31/148* (2013.01); *D04H 1/4391* (2013.01); *D04H 1/728* (2013.01); *A61F 2210/0004* (2013.01); *A61F 2210/0076* (2013.01); *A61F 2230/0069* (2013.01); *A61L 2300/21* (2013.01); *A61L 2300/412* (2013.01); *A61L 2430/22* (2013.01)

(58) Field of Classification Search
CPC .......... A61L 27/34; A61L 27/58; A61L 27/50; A61L 27/56; A61L 27/18
USPC .......................................................... 623/1.2
See application file for complete search history.

(56) References Cited

U.S. PATENT DOCUMENTS

| | | | | |
|---|---|---|---|---|
| 9,849,007 | B2* | 12/2017 | Kaufmann | A61L 27/56 |
| 2003/0036794 | A1 | 2/2003 | Ragheb et al. | 623/1.15 |
| 2005/0009178 | A1 | 1/2005 | Yost et al. | 435/399 |
| 2005/0271061 | A1 | 12/2005 | Cottone et al. | 424/426 |
| 2007/0269481 | A1 | 11/2007 | Li et al. | 424/423 |
| 2008/0299164 | A1 | 12/2008 | Trollsas | 424/422 |
| 2009/0018643 | A1 | 1/2009 | Hashi et al. | 623/1.15 |
| 2011/0301696 | A1 | 12/2011 | Mangiardi | 623/1.46 |

OTHER PUBLICATIONS

Eliason, J.L. and W.D. Clouse "Current Management of Infrarenal abdominal aortic aneurysms" Surgical Clinics of North America, 2007. 87: p. 1017-1033.
Starnes, B.W., N.T. Tran, and J.M. McDonald "Hybrid Approaches to Repair of Complex Aortic Aneurysmal Disease" Surgical Clinics of North America, 2007. 87: p. 1087-1098.
Li, W.-J., et al. "Electrospun nanofibrous structure: A novel scaffold for tissue engineering" Journal of Biomedical Materials Research, 2001. 60: p. 613-621.
Lannulli, J., et al., "Electrospinning for tissue engineering scaffolds" Materials Science and Engineering C, 2007. 27: p. 504-509.
Kwon, I.K., S. Kidoaki, and T. Matsuda "Electrospun nano-to microfiber fabrics made of biodegradable copolyesters: structural characteristics, mechanical properties and cell adhesion potential" Biomaterials, 2005. 26: p. 3929-3939.
Doshi, J and D.H. Reneker "Electrospinning Process and Applications of Electrospun Fiber" Journal of Electrostatics, 1995. 35: p. 151-160.
Reneker, D.H. and A.L. Yarin, Electrospinning jets and polymer nanofibers. Polymer, 2008. 49: p. 2387-2425.
Deitzel, J.M., et al., The effect of processing variables on the morphology of electrospun nanofibers and textiles. Polymer, 2001. 42: p. 261-272.
Taylor, G., Electrically Driven Jets. Proceedings of the Royal Society of London. Series A, Mathematical and Physical Sciences, 1969. 313(1515): p. 453-475.
Tillman, B.W., et al., The in vivo stability of electrospun polycaprolactone-collagen scaffolds in vascular reconstruction. Biomaterials, 2009. 30: p. 583-588.
Lee, S.J., et al., Development of a composite vascular scaffolding system that withstands physiological vascular conditions. Biomaterials, 2008. 29: p. 2891-2898.
Thompson, C.J., et al., Effects of parameters on nanofiber diameter determined from electrospinning model. Polymer, 2007. 48: p. 6913-6922.
Reneker, D.H., et al., Nanofiber garlands of polycaprolactone by electrospinning. Polymer, 2002. 43: p. 6785-6794.
Yoshimoto, H., et al., A biodegradable nanofiber scaffold by electrospinning and its potential for bone tissue engineering. Biomaterials, 2003. 24: p. 2077-2082.
Mo, X.M., et al., Electrospun P(LLA-CL) nanofiber: a biomimetic extracellular matrix for smooth muscle cell and endothelial cell proliferation. Biomaterials, 2004. 25: p. 1883-1890.
Beachley, V. and X. Wen, Effect of electrospinning parameters on the nanofiber diameter and length. Materials Science and Engineering C, 2009. 29: p. 663-668.
Tan, E.P.S., S.Y. Ng, and C.T. Lim, Tensile testing of a single ultrafine polymeric fiber. Biomaterials, 2005. 26: p. 1453-1456.
Gaumer, J., et al., Structure-function relationships and source-to-ground distance in electrospun polycaprolactone. Acta Biomaterialia, 2009. 5(5): p. 1552-1561.
Theron, S.A., E. Zussman, and A.L. Yarin, Experimental investigation of the governing parameters in the electrospinning of polymer solutions. Polymer, 2004. 45: p. 2017-2030.
Duling, R.R., et al., Mechanical Characterization of Electrospun Polycaprolactone (PCL): A Potential Scaffold for Tissue Engineering. Journal of Biomechanical Engineering, 2008. 130.
International Search Report and Written Opinion for PCT Patent Application No. PCT/US2013/025829 dated Jun. 2, 2013.
Venugopal et al., "Interaction of cells and nanofiber scaffolds in tissue engineering" Journal of Biomedical Materials Research Part B: Applied Biomaterials, vol. 84, No. 1, pp. 34-48 (2008).
Nottelet et al., "Factorial design optimization and in vivo feasibility of poly(e-caprolactone)-micro- and nanofiber-based small diameter vascular grafts" Journal of Biomedical Materials Research Part A, vol. 89, No. 4, pp. 865-875 (2009).
Sill et al., "Electrospinning: applications in drug delivery and tissue engineering" Biomaterials, vol. 29, No. 13, pp. 1989-2006 (2008).
International Search Report and Written Opinion for PCT Patent Application No. PCT/US2011/028201 dated Dec. 7, 2011.
EP Extended Search Report for Patent Application No. 13748603.1 dated Aug. 27, 2015.
AU Patent Examination Report No. 1 for Patent Application No. 2013221777 dated Oct. 23, 2015.
JP Office Action for Patent Application No. 2014-556808 dated Jan. 10, 2017.
AU Patent Examination Report No. 1 for Patent Application No. 2017200200 dated Feb. 21, 2018.

* cited by examiner

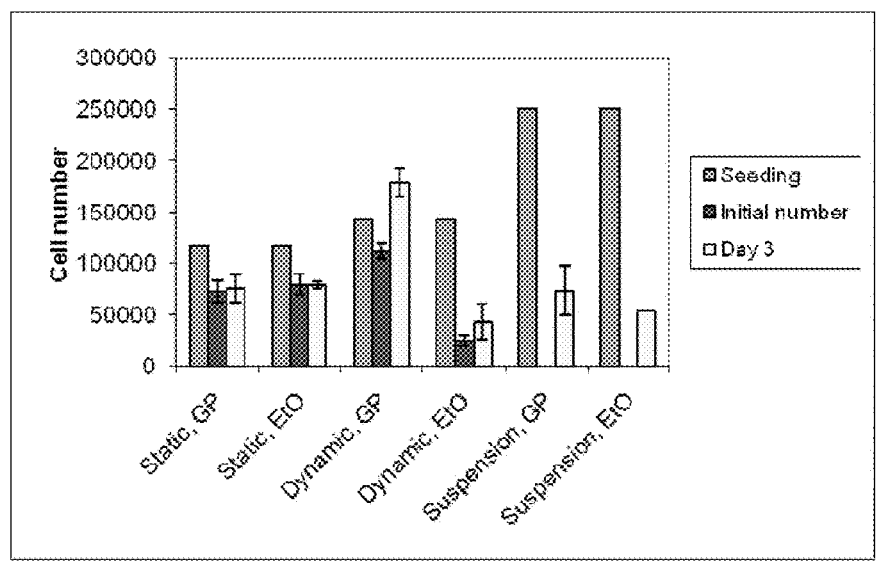
FIG. 9
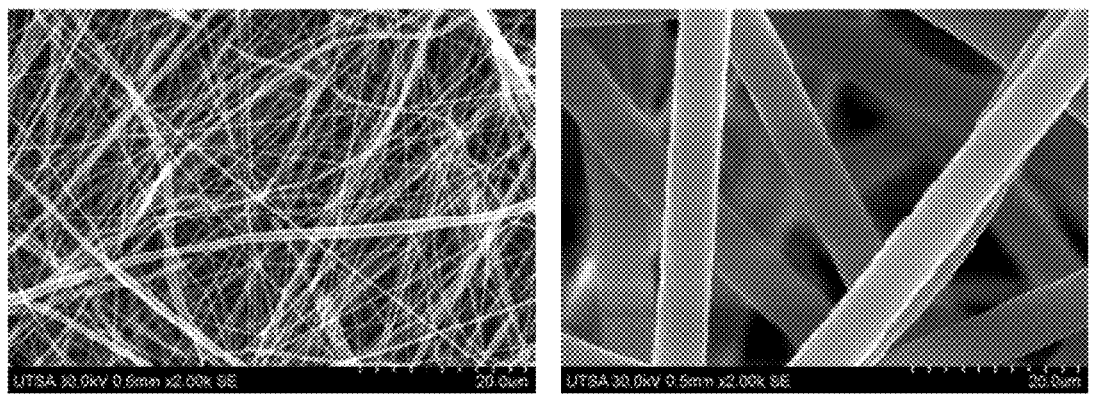
FIGS. 10A-B

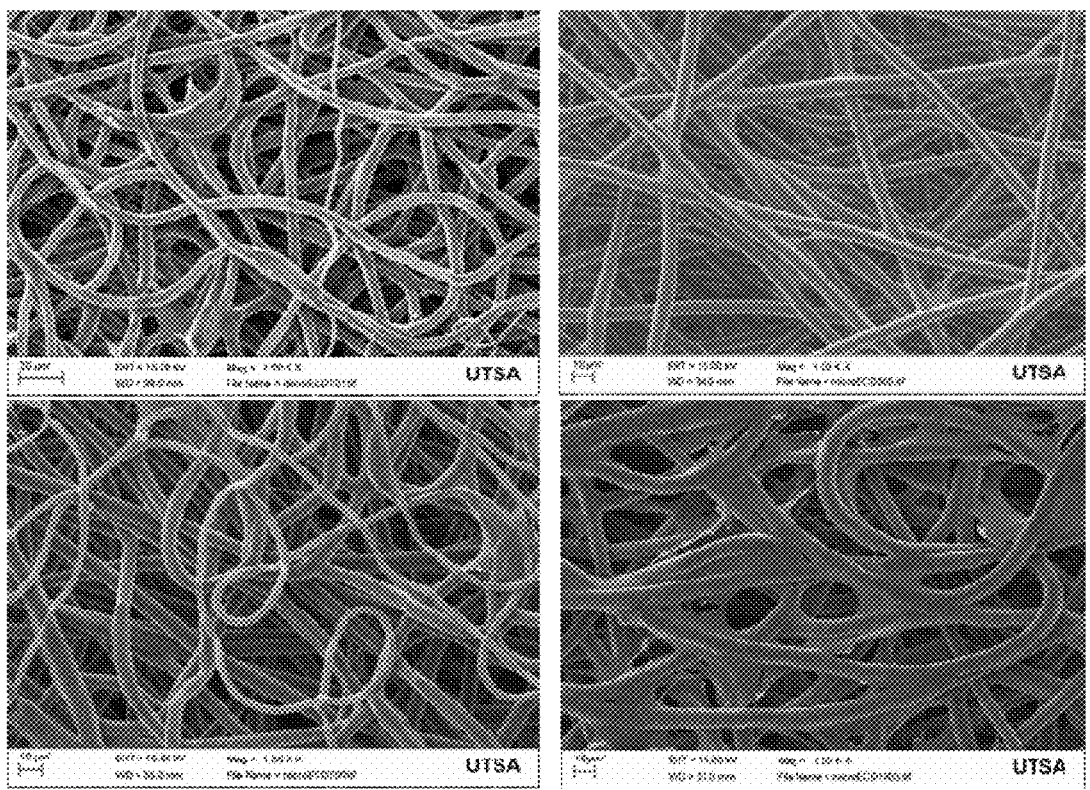
FIGS. 13A-D

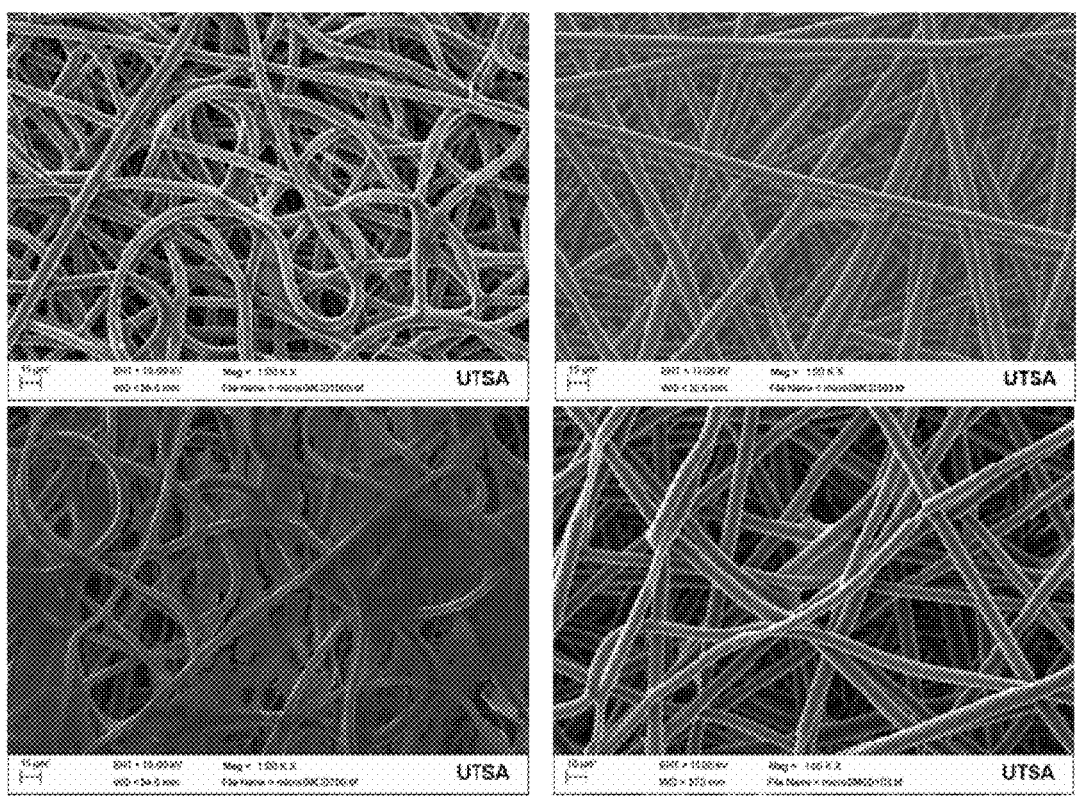
FIGS. 14A-D

SCAFFOLD SYSTEM FOR TISSUE REPAIR

PRIORITY CLAIM

This application is a continuation application of U.S. patent application Ser. No. 15/043,968, filed Feb. 15, 2016, which is a continuation from U.S. patent application Ser. No. 13/766,530 entitled 'Scaffold System for Tissue Repair" to Massey et al., filed Feb. 13, 2013 which claims priority to U.S. Provisional Application No. 61/598,125 entitled "Scaffold System to Repair Cardiovascular Conditions" to Massey et al., filed Feb. 13, 2012, all of which are incorporated herein by reference.

BACKGROUND OF THE INVENTION

1. Field of the Invention

The invention generally relates to and methods for the treatment of cardiovascular, endovascular and endoluminal conditions. More specifically, the invention relates to the treatment of aneurysms or other damaged complex tissue.

2. Description of the Relevant Art

Abdominal aortic aneurysms, commonly referred to as AAA, consist of a 50% enlargement of the abdominal aorta which is believed to be caused by the breakdown of the tunica media, a vessel wall layer primarily composed of smooth muscle cells. While the exact cause of AAA is not well understood, it is believed to be a complex process involving hemodynamic forces as well as local extracellular matrix remodeling, infiltration of macrophages and lymphocytes and increase in matrix metalloproteinase enzymes which all play a role in the destruction of elastin fibers and smooth muscle cells. Over time, a gradual reduction of medial elastin fibers, thinning collagen within the media and thickening of the intima heighten the aneurismal tendency. Loss of elasticity and strength of the tunica media along with compensatory collagen production lead to arterial expansion, forming an aneurysm. Histologically, the aneurysm elastin fragmentation, chronic transmural inflammation, and depletion of smooth muscle cells are observed. Aneurysm progression is characterized by molecular mediators and extracellular matrix-degrading proteinases including matrix metalloproteinases 2 and 9. Increased collagen turnover has been targeted as a potential cause of aneurysm growth and rupture.

Studies show that 3% of all individuals aged 50 and over, predominately males, have AAA. In addition, 2.1% of men over 65 years of age will die of ruptured aortic aneurysms. The average aorta at the renal level is approximately 2 cm in diameter; therefore, an aneurysm is technically a 3 cm dilation. By the age of 65, 5% of men and 1.7% of women have an aortic diameter of at least 3 cm. The prevalence of AAA greater than or equal to 3 cm increases 6% with each decade beyond 65 years of age. However, most aneurysms are not considered clinically relevant until they reach 4 cm, and surgery is generally not prescribed until they are approximately 5 cm. The risk of rupture is known to increase with the diameter of the aneurysm. Only 25% of patients with ruptured aneurysms reach the hospital and only 10% make it to the operating room. Because of such high mortality rates, it is important to treat the aneurysm before it ruptures.

Current treatment of the AAA includes either open surgery or endovascular aneurysm repair, depending on the patient physiology and pathology. Open surgical treatment of aneurysms was first performed by Dubost and colleagues in 1951 but was reintroduced by Charles Rob in 1963 using the current retroperitoneal approach. With the retroperitoneal approach, the aneurysm is accessed no higher than the 11th rib when the patient is prone. An alternative open surgical method is the transperitoneal technique in which the aneurysm is accessed through an incision along the midline. In 1991, an alternative approach to the open surgical method was introduced by Juan Parodi in which iliofemoral access was used to insert an endovascular graft to cover the aneurysm: endovascular aneurysm repair (EVAR).

EVAR utilizes stent technology to place the graft over the aneurysm and into the iliofemoral arteries, splitting at the bifurcation. The graft serves to block off the aneurismal segment of the aorta without extensive damage to the arteries. Currently FDA approved stent-grafts contain either a woven polyester (PET) or ePTFE graft on a stainless steel, a Cobalt-Chromium alloy, or Nitinol stent. The grafts are fixated using either self-expansion, stents, barbs, or a combination of these. However, because the graft is meant to separate the unhealthy portion from the blood flow, inherent problems exist in the implementation. Tortuosity of the aorta and iliac bifurcation, particularly an angulation of 90° or greater, may lead to an endoleak after implantation in which blood seeps between the graft and the lumen of the aorta, reaching the aneurysm. Calcification and thrombotic events also play a role in limiting EVAR effectiveness, particularly when calcification is greater than 50% or thrombosis is 25%-50%. Success of an EVAR graft is usually defined by the absence of any of the four types of endoleaks. Type I endoleak occurs when blood flows between the graft and the vessel wall at either the proximal or distal ends of the graft. When blood flows into the aneurysm sac from branch vessels, it is considered a Type II endoleak. Type III endoleaks are the result of poor anastomoses between different sections of the graft. If leakage occurs through the graft material, it is considered a Type IV endoleak. Types II and IV generally resolve spontaneously while Types I and III pose a greater danger and must be repaired during a subsequent procedure.

Testing endovascular grafts for treatment of AAA require first, appropriate cell culture evaluation in vitro and structural mechanical properties tests, then an appropriate AAA animal model in order to be properly assessed, particularly in terms of coagulation and fibrinolytic systems. Both canine and swine models are considered appropriate for testing current EVAR devices.

SUMMARY OF THE INVENTION

A device for tissue repair includes an expandable scaffold positionable in a portion of a luminal tissue structure of a mammal. The scaffold comprises a first surface comprising substantially curvilinear fibers and a second surface comprising substantially linear fibers. In some embodiments, the first surface is a concave surface, and the second surface is a convex surface. When the scaffold is positioned within a luminal tissue structure of a mammal, the first surface of the scaffold provides an appropriate surface for cell attachment while the second surface of the scaffold facilitates the ingress and organization of cells. In some embodiments, the first surface is an opposing surface to the second surface.

The device may be used for various tissue repairs. Ideally the device is used to repair vascular tissue, however, the device may be used for other luminal tissue structures such as the esophagus, gastrointestinal tract, the heart, reproductive organs, urologic organs or passages, oral/nasal/pharyngeal structures, respiratory tract structures, the lymphatic system, and the kidneys. Luminal tissue structures may also include artificially or unnaturally created hollow structures or conduits such as those created with surgical interventions or trauma. In some embodiments, the device may be configured for use to repair an aneurysm. In other embodiments the device may be configured for use to repair a void or semi-void space in a luminal tissue structure.

The scaffold is preferably composed of one or more poly(α-hydroxy esters). An exemplary poly(α-hydroxy esters) is polycaprolactone. In some embodiments, the scaffold is composed of natural polymers that are biodegradable and/or bioresorbable. Examples of natural polymers that are biodegradable and/or bioresorbable include, but are not limited to elastin, collagen, DNA, RNA, glucosaminoglycans, or mixtures thereof.

In an embodiment, the scaffold is supported by a supporting structure. The supporting structure may be expandable (e.g., an expandable stent). The supporting structure may be a pliant structure (i.e., a structure that is not rigid). The supporting structure may be a repositionable structure. The supporting structure may be bioresorbable and/or biodegradable.

The scaffold may be composed of nonwoven microfibers and/or nanofibers which may be electrospun from a biodegradable material and/or a bioresorbable material compound. Alternatively, the fibers may be fabricated using drawing, extrusion and/or pultrusion techniques. In some embodiments, the scaffold is substantially tubular. The scaffold may be supported by at least a portion of a medical device. The scaffold may be sutured or mechanically affixed to a supporting structure. Alternatively, the scaffold may be chemically adhered to a supporting structure.

The scaffold may be directly or indirectly electrospun or formed onto a supporting structure. The supporting structure may be at least partially incorporated into the electrospun scaffold.

A method of repairing tissue includes: inserting a device into a hollow, void or semi-void tissue structure, wherein the device comprises an expandable scaffold, wherein the scaffold comprises a first surface comprising substantially curvilinear fibers and a second surface comprising substantially linear fibers; expanding the scaffold such that the scaffold contacts at least a portion of the tissue structure, wherein the scaffold is positioned such that the concave surface of the scaffold is aligned with the lumen of the tissue structure providing an appropriate surface for cell attachment while the less concentrated convex surface facilitates the ingress and organization of cells; and securing the device in the tissue structure.

In another embodiment, a device for treating a medical condition includes an expandable scaffold, wherein the scaffold comprises a concave surface comprising substantially curvilinear fibers and a convex surface comprising substantially linear fibers.

Cardiovascular, endovascular and endoluminal conditions may be treated by inserting the device into the affected area expanding it to provide a template for and to encourage regrowth of the damaged tissue. It is initially secured using a supporting structure, then relies on a more integrated fixation. An integrated fixation includes tissue and/or biological fixation.

BRIEF DESCRIPTION OF THE DRAWINGS

Advantages of the present invention will become apparent to those skilled in the art with the benefit of the following detailed description of embodiments and upon reference to the accompanying drawings in which:

FIG. 9 depicts a graph comparing human aortic smooth muscle cells using different sterilization and seeding techniques;

FIGS. 10A-B depicts SEM images of electrospun scaffolds A (nano) and B (micro) at 2000×;

FIGS. 13A-D depicts SEM images of electrospun microfibers with human aortic endothelial cells on days 1, 3, 7 and 10;

FIGS. 14A-D depicts SEM images of electrospun microfibers with human aortic smooth muscle cells on days 1, 3, 7 and 10;

Figure 1:
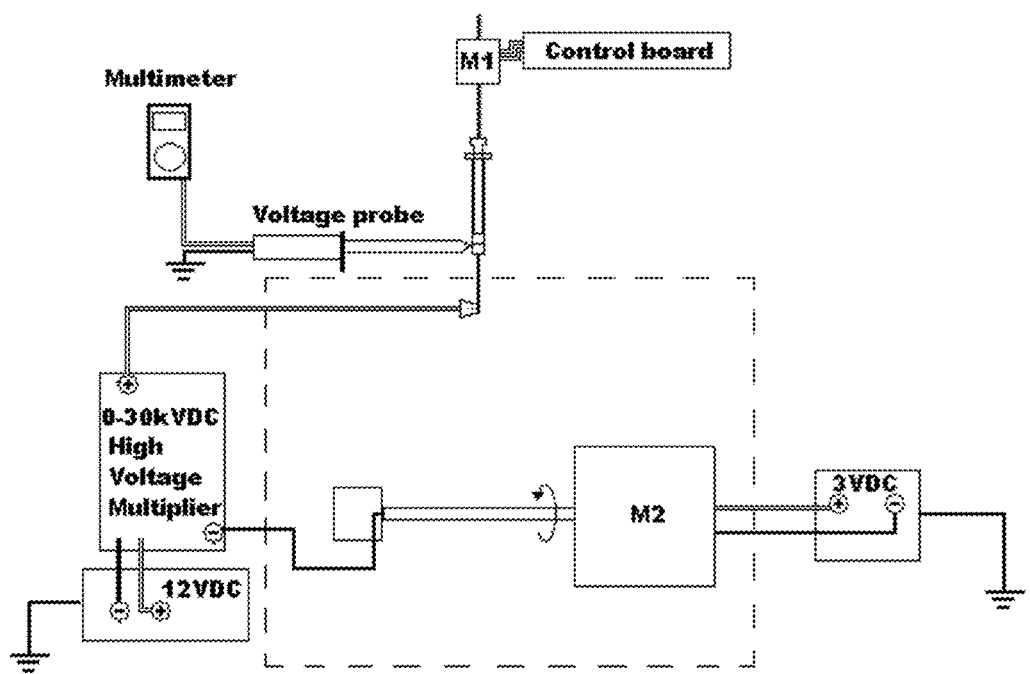
FIG. 1 depicts a schematic diagram of an electrospinner.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise.

As used herein the term "luminal tissue structure" refers to tissue structures or organs within a mammal which are hollow, void or semi-void structures or organs and/or conduits having a luminal surface. The luminal tissue structures may support the transport of fluids (gasses or liquids). Examples of luminal tissue structures include, but are not limited to blood vessels (arteries and veins), the heart, fistulas, the esophagus, the gastrointestinal tract, female reproductive organs, urologic organs or passages, sinuses, structures and/or passages in the ear, the mouth, nasal passages, the lungs, the throat, trachea, bronchial tubes, the lymphatic system, and/or the kidneys. Luminal tissue structures may also refer to artificially or unnaturally created hollow structures or conduits such as those created with surgical interventions or trauma.

The term "tissue repair" refers to repairing thin tissue, complex tissue, voids or semi-voids formed in tissue. Examples of conditions that require tissue repair include, but are not limited to cardiovascular conditions (e.g., aneurysms), endovascular conditions, endoluminal conditions, conditions associated with surgical interventions, conditions associated with cancerous tissue, conditions associated with wounds or penetrations.

EVAR utilizes stent technology to place a graft over an aneurysm from within the blood vessel, essentially blocking off the aneuyrsmal sac from blood flow. Many of the risks associated with EVAR are due to the permanent introduction of a material that is not bioactive. Such risks may be circumvented using a tissue engineering approach to treat vascular conditions. Tissue engineering is a means of rebuilding a tissue by introducing a scaffold which is seeded with cells into a defect area. Alternatively, the scaffold may be placed within a mammal and self-seeded meaning cells are not added prior to scaffold placement but attach after scaffold placement. The scaffold provides a three dimensional structure on which the cells can proliferate and organize into a new tissue. Changing the scaffold properties alters the way the cells grow and organize. Taking a tissue engineering approach to tissue repair would allow native cells to infiltrate the scaffold and remodel into a tissue structure of appropriate anatomic and/or biologic conditions.

Applying concepts of tissue engineering, our system uses a porous/fibrous scaffold placed into the luminal tissue structure and seeded naturally by infiltrating cells. This allows for the tissue to be "repaved" as the cells secrete extracellular matrix components and organize in response to the scaffold morphology. Infiltrating cells will come from both the blood flowing through the scaffold as well as the surrounding tissue. Initially, the cells act according to the wound healing response. Then the initially adhered cells signal for other more appropriate cells to adhere and migrate through the scaffold.

As different cells adhere, migrate and proliferate a remodeling process takes place in which extracellular matrix components and scaffold fibers are broken down in some areas and bolstered in others. Therefore, as time progresses the scaffold is slowly replaced by functional tissue organized in response to physiological conditions. Eventually the scaffold will be completely degraded leaving tissue in its place of the correct shape and containing vital components such as collagen, elastin and vasa vasorum. At this point the condition in need of repair will be minimized or no longer present.

By placing the scaffold within a luminal tissue structure, it is able to reduce the effect of mechanical stimuli while concomitantly providing a structure with high porosity on which appropriate cells can adhere, migrate, proliferate and organize into a new tissue. In addition, the infiltration of cells increases the scaffold strength, compliance and integration into the existing tissue. In one embodiment, this reduces the chances of endoleaks present in current EVAR stent-grafts. As the tissue wall remodels, the scaffold degrades allowing the new tissue to take over both form and function.

Unlike current treatments which try to present an impermeable barrier, the scaffold disclosed herein will initially be permeable to allow cell infiltration. Once appropriate cells adhere, put down extracellular matrix components and proliferate, the scaffold will become substantially impermeable. Furthermore, in an embodiment, the scaffold is biodegradable, so that as new tissue is formed, the scaffold will slowly be broken down by natural metabolic pathways.

Unlike current tissue engineered structures (such as blood vessels), the described device may be positioned within the damaged tissue with minimum excision or damage to surrounding tissue.

In an embodiment, scaffolds intended for use in an engineered blood vessel or other luminal tissue structures have: a porosity and surface area conducive to cell migration, proliferation and differentiation; stiffness and mechanical strength congruent to native tissue; and a biodegradation rate coinciding with tissue formation.

In an embodiment, a scaffold that is intended for the aorta is configured to be implanted endovascularly. A stent, or other supporting structure, for deployment in an aorta is inserted using a catheter in the femoral artery and expanded to the nominal size of the aorta at the aneurysm site. In an embodiment, the scaffold includes a material that can withstand the 5-6× expansion of the stent in the aorta which is necessary for an EVAR procedure. Furthermore the scaffold includes a material that degrades and losses mechanical properties as the tissue is developed allowing the mechanical stresses to gradually be transferred to the new tissue.

In an embodiment, a scaffold includes a biodegradable material and/or a bioresorbable material. Polymers may be chosen based on water permeability, crystallinity, glass transition temperature, and degradation time.

In one embodiment, the scaffold is composed of nonwoven polycaprolactone (PCL) fibers. PCL is a biodegradable material commonly used in FDA approved clinical applications based on its strength, elastic properties, and extended degradation time. Other polymers, copolymers or polymer blends which may be used as a scaffold include, but are not limited to, Poly(α-hydroxy esters) such as polylactic acid (PLA), polyglycolic acid (PGA) poly (D,L-lactide-co-glycolide) (PLGA), polydioxanone (PDO), Poly (4-hydroxybutyric acid) (P4HB).

PGA is a widely used bioresorable aliphatic polyester commonly used in FDA approved sutures. PGA may have average biocompatibility and consistent mechanical properties, which makes PGA acceptable for tissue engineering applications. The in vivo degradation rate of PGA is reported to be 2-4 weeks. PGA has a crystallinity of 46-52%, a melting point ($T_m$) of 225° C. and has a low solubility in organic solvents. Due to its high crystallinity, PGA is soluble in highly fluorinated organic solvents. The hydrophilic polymer is especially susceptible to hydrolytic degradation, which accounts for 60% loss in strength in 2 weeks as well as a marked decrease in local pH and crystallinity. The glass transition temperature ($T_g$) of PGA is near physiologic temperature, which contributes to the water diffusion and the resulting hydrolysis in vivo. PGA is a good choice for applications requiring high initial toughness and fast degradation.

PLA is also a bioresorbable aliphatic polyester synthesized as either the D(−), L(+) or D,L isomers based on the position of a methyl group in the monomer. PLA is more hydrophobic than PGA due to the methyl group, which increases its solubility in organic solvents and decreases its rate of hydrolysis (30-50 weeks). The crystallinity of PLA is approximately 37% and the $T_m$ is 96° C. Like PGA, PLA is also commonly used in medical applications.

Polycaprolactone (PCL) is a semicrystalline, hydrophobic, bioresorbable, aliphatic polyester and demonstrates high elasticity with slow degradation (1-4 years). The $T_m$ of PCL is 60° C. and the $T_g$ is −60° C. but the decomposition temperature is 350° C. Hydrolytic degradation of PCL occurs in the amorphous regions of the bulk material by random chain scission of ester groups as a result of loose structural packing in these regions. The result of the cleaved ester bonds is capronic acid, which can be a catalyst for further degradation if not removed. The cleaved chains, however, can rearrange and lead to ordered packing that maintains or increases the crystallinity. The degradation rate of PCL can also be affected by the structural and morphological forms as well as the surface area to volume ratio. Fibrous PCL has been reported to have a relatively low Young's modulus but a higher yield stress due to its increased yield strain. When comparing PDLLA, PLLA and PCL, it was determined that PDLLA and PLLA exhibited higher tensile modulus but PCL exhibited higher percentage elongation at break.

Copolymers and polymer blends allow for properties to be tailored to a specific application, with the percentage of each dependent on the desired properties of the copolymer. For example, poly(lactic-co-glycolic acid) (PLGA) which is an amorphous polymer because the PGA and PLA chains are not tightly packed.

Polydioxanone (PDO) is a biodegradable polymer with high crystallinity (55% crystalline fraction) and a degradation rate between PLA and PGA. A unique property of PDO is its shape memory. The bulk material properties of PDO are similar to structural components of native ECM.

Poly (4-hydroxybutyric acid), a homopolymer of 4-hydroxybutyrate (4HB), and belongs to a diverse class of materials called polyhydroxyalkanoates (PHAs) that are produced naturally by microorganisms. The polymer is a thermoplastic linear polyester and is produced by means of a recombinant fermentation process. Following fermentation the polymer is isolated and purified to yield an extremely high purity material.

Polymers which degrade through hydrolysis of their ester bond into acidic monomers, can be removed from the body through normal metabolic pathways, thus making them suitable to biodegradation and/or bioresorbable applications. The synthetic nature of PCL makes it more easily tailored for a particular application due to its consistency. Natural polymers such as collagen, elastin or DNA may also be used for this application.

In addition to choosing a feasible material, the scaffold manufacturing process must be appropriate for the given application. In an embodiment, electrospinning is used for manufacturing nonwoven fibers. Electrospinning is a fiber manufacturing process using electrostatic forces to form nonwoven fibers. A high voltage of one polarity is applied to a polymeric solution or melt, which causes coulombic repulsion as the concentration of positive ions exceeds negative ions. As the solution or melt is expelled and the voltage is applied, the similar charges within the expelled droplet repel each other. The combination of the repulsion within the expelled droplet and the attraction to the collector allows the molecules within the droplet to overcome the surface tension that maintains the droplet form. A jet of solution then accelerates towards the collector, allowing the volatile solvent to evaporate in the distance between the tip of the spinneret and the collector plate. When a fluid is expelled at a sufficient rate and a potential greater than the threshold is applied, the jet is continuous and forms continuous nonwoven fibers ranging from a few nanometers to a few micrometers on the collecting unit. Electrospinning polycaprolactone yields a compliant nonwoven textile well suited for use in vascular scaffolds due to the potential for high porosity and fiber sizes comparable to extracellular matrix components as well as its degradation and mechanical properties. By changing the processing parameters or collecting unit, a myriad of different scaffolds may be formed.

Electrospinning process parameters have a significant effect on the resultant fiber diameter and consistency. In order to prepare a scaffold for use in vascular repair, it is desirable to understand how those parameters affect properties of the resultant scaffolds that will play a role in cell proliferation and the success of the scaffold in general. Electrospinning relies on appropriate combinations of a number of parameters including solution concentration, extrusion rate, applied voltage, tip to collector distance, temperature, humidity, volatility of solvent, and polymer characteristics. The effect of these parameters on the properties of electrospun polycaprolactone was studied.

In one embodiment, techniques including but not limited to pultrusion, drawing, or extrusion may be optimized for manufacturing the scaffold.

In one embodiment, once produced the scaffold may be gas plasma treated in order to introduce moieties on the surface that are conducive to cell infiltration and proliferation. Gas-plasma treatment of a scaffold may include subjecting the scaffold to a plasma formed by a reactive gas. A reactive gas may include oxygen, nitrogen, argon, ammonia or combinations thereof.

The scaffold may be treated with chemical stimuli including but not limited to Platelet Derived Growth Factor (PDGF), Vascular Endothelial Growth Factor (VEGF), Angiotensin II (Ang II), Collagen VIII, Collagen I or Collagen V.

In certain embodiments, the scaffold may have a coating or incorporate a drug in the implant itself to provide the release of a pharmaceutical agent, which may encourage the adhesion of the stent in place, may induce cell ingrowth, may enhance tissue healing, etc. In exemplary embodiments, the coating or incorporated drug may be biocompatible. In certain embodiments, the coating is a polymeric coating. In certain embodiments, the coating is a polymeric coating that includes a therapeutic agent. Classes of therapeutic agents that may be delivered by the stent include DNA, RNA, nucleic acids, proteins, peptides, or small molecules. Exemplary therapeutic agents include antibiotics, anti-inflammatory agents, corticosteroids, vasoconstrictors, vasodilators, etc. In certain embodiments, the coating or incorporated drug may include retinoic acid to enhance vascular wound healing.

A supporting structure (e.g., a stent) may be used to deploy and support the scaffold in the luminal tissue structure. In one embodiment, the scaffold may be attached to a stainless steel, cobalt-chromium alloy, Nitinol, or polymeric stent. The scaffold may be sutured, mechanically adhered, or chemically adhered directly to a stent or other type of structural support. In some embodiments, the scaffold is directly or indirectly electrospun onto the supporting structure. In an embodiment, a supporting structure may be incorporated into the electrospun scaffold. Alternative setups may include spinning the fibers directly onto the stent; altering the polymer used; using a different solvent; using barbs instead of a stent; using a repositionable structure or a structure that is not a stand-alone stent. Each of these setups would essentially be designed using the same embodiment as the original but would implicate minor changes to the deployment or degradation characteristics of the supporting structure.

Supporting structures, in some embodiments, may be formed from a biodegradable and/or bioresorbable material. In this manner, the stent will eventually be removed by the body.

After the scaffold system is expanded in the luminal tissue structure, cells from the fluids passing through the tissue as well as from the native vessel will infiltrate the scaffold as a result of the normal wound healing response. Because the scaffold is in an expanded form, the fibers will be aligned somewhat concentrically allowing the cells to orient along the same direction. In one embodiment, the orientation of smooth muscle cells would be similar to native tunica media. Fluid flow will instigate cells oriented in the direction of the flow. In one embodiment, endothelial cells will orient with blood flow to form a new endothelium. Over time, the biomaterial scaffold may be hydrolytically degraded and disposed of through natural metabolic pathways leaving new tissue in its place. Because the cells will infiltrate the scaffold, the resulting graft will be directly connected to native tissue. In one embodiment, the direct connection may reduce or eliminate the occurrence of endoleaks unlike current stent-graft systems. In addition, the reinforcement provided by collagen and other extracellular matrix components may contribute to increased stiffness and strength of electrospun scaffolds observed when cells are present. In an embodiment, tissue remodeling may allow collateral vasculature to attach to the new vessel wall, unlike currently used stent grafts.

Investigating interaction of various cells on electrospun fibers, it has been observed that scaffolds made of polymers more resistant to degradation and containing sufficient porosity promote cell integration and proliferation purportedly due to the 3-dimensional structure. This supports the widely held assumption that three-dimensional as opposed to two-dimensional surfaces are preferred by cells over a period of time.

In one embodiment fibers within the scaffold may range in diameter (<200 nm to >10 pin) and may be arranged to display different porosities (e.g., 70-85% porous) to accommodate different cell types and attachment tendencies. In addition, the fiber orientation has been noted to play a role in cell adhesion, migration and proliferation. Cells located within arranged fibers frequently display a similar orientation—a characteristic which may be utilized for growing aligned tissues. Investigating cell response to aligned verses nonaligned fibrous scaffolds shows that when fibroblasts were cultured on aligned as opposed to non-aligned polyurethane (PU) fibers, there was an increased amount of collagen produced on the aligned scaffolds, although no increase in cell number was detected. The fiber concentration per area and fiber curviness may alter the cell attachment, proliferation and remodeling. Therefore, in one embodiment, scaffolds may be designed to include a morphological gradient from the concave to the convex side. The concave side, for example, may include fibers with a more looped appearance (e.g., curvilinear fibers), while the convex side includes fibers that are more linear. This morphological difference may aid in organization of different cell types throughout the scaffold without the need of an additional structure. In addition, the change may aid in reducing blood flow across the scaffold, therefore reducing mechanical force on the aneurysm and reducing the chance of rupture.

Current stent-graft technology uses more bioinert materials, which may result in a fibrous capsule as a result of the immune response. The described embodiments encourage the graft to endothelialize so that it is not rejected (i.e., encapsulated). In one embodiment, a scaffold graft, formed as described herein, may utilize the immune response by providing a means for the cells to attach, migrate and proliferate in an organized manner. The gradient comes into play with the cells when the endothelial cells attach to the curvilinear fibers of the concave surface—which have more potential points of contact without compromising porosity. The endothelial cells prefer to grow in a single layer so the concentration of fibers may aid in their attachment and communication. Meanwhile, the convex, more linear, less concentrated side is designed for smooth muscle cells which prefer to organize in striations and follow the length of the fiber. The linearity of the fibers may aid in their organization into circumferential striations. By providing a scaffold designed for cells as opposed to an inert surface, complications may be decreased. The scaffold grafts described herein may allow for the blood vessels (e.g., blood vessel that supply blood to the aorta) to develop out of necessity. This is, generally, not possible with the current technology which simply blocks off these vessels and potentially leads to burst sacs if one of these is supplying blood to the sac.

To tailor the scaffolds for a particular application, the solution concentration, applied voltage, and extrusion rate on tensile stress and strain, porosity and fiber morphology may be changed individually or collectively.

In all the work described herein, the electrospinner used was a custom built model consisting of a 0-30 kV voltage source (Information Unlimited) attached to a 22Gs, 2" blunt needle (Hamilton) on a 2.5 mL gas tight syringe (Hamilton). The needle was positioned 10 cm above the collecting unit and the environmental conditions within the electrospinning equipment were maintained in the range: 23-25° C. and 45-55% humidity. A schematic of the electrospinner are shown in FIG. 1. The syringe was depressed with a non-captive bipolar linear actuator (Haydon Switch and Instruments) controlled with a bistep controller (Peter Norberg Consulting, Inc.) using serial commands input through the Hyperlink terminal feature of the PC. In the preliminary work, serial commands of 50r, 125r and 200r were used to define the run rate in microsteps/s/s in order to slew the motor. This produced polymer solution flow rates of 0.012 mL/min, 0.029 mL/min and 0.047 mL/min. The positive terminal of the high voltage source was connected via a small alligator clip approximately 3 mm from the tip of the needle. For flat scaffolds, a collecting plate consisting of replaceable aluminum foil over an aluminum screen was connected to the negative terminal of the voltage source and is positioned from the tip of the needle using a screw sensitive to under 1 mm. When tubular scaffolds were made, the aluminum foil and screen were replaced by an aluminum mandrel system. The mandrel was composed of a 0.5 diameter aluminum rod attached to the negative terminal through a bushing. It was turned using a 12 VDC permanent magnet motor (Grainger) which was operated using only 3 VDC to give 587.5 RPM. The spinning area was enclosed by an acrylic case to reduce external interference. Scaffolds were stored in individual vials at room temperature under vacuum at 634.92 mmHg (25 inHg). Both the flat and tubular scaffolds were classified by their manufacturing parameters to determine how these parameters affect mechanical properties. In addition, the effect of the manufacturing parameters on porosity and degradation for the tubular scaffolds was explored.

Electrospinning parameters were optimized to determine which setup provides the best tensile strength and expansion characteristics. After initial testing of a wider range of tip to collector plate distances, solution concentrations and applied voltages, an experiment was setup to examine parameters with the most potential. Samples were made using polycaprolactone (Mn 80000 kDa, Aldrich) dissolved in chloroform (>=99.8% HPLC grade; Sigma-Aldrich). Concentrations of 8 wt %, 10 wt % and 12 wt % concentrations were used for flat scaffolds while 10 wt %, 12 wt % and 14 wt % solutions were used for tubular scaffolds. Each solution was used within 24 hours and stored in sealed amber bottles between uses.

For the flat scaffolds, 8 kV, 11 kV, 14 kV and 17 kV voltages were applied to each concentration and the syringe was depressed with the 50r serial command corresponding with a 0.012 mL/min flow rate. In addition to a 50r input, the 12 wt % solution was also spun using 125r and 200r commands for the same voltages. This allowed for analyses of the effect of concentration on the resulting scaffolds as well as the effects of voltage and flow rate.

Each flat sample was approximately 0.3 mm thick and cut for mechanical testing using a straight razor blade. The exact thickness and width of each sample was measured by placing the samples between two glasses slides and using calipers to determine the thickness then subtracting the thickness of the slides. This information was used when determining the stress values during mechanical testing. The average fiber diameter, distribution of fiber sizes and sample morphology was analyzed using SEM. For the tubular scaffolds, transverse strips were cut so that the extension axis when tested corresponded with the circumferential stress associated with uniformly expanding the tubular scaffolds. Two straight razor blades were affixed parallel, 0.5 cm apart, allowing consistent strips to be cut without dragging the blade across the samples. Prior to testing, the width and thickness of each strip were measured using an inverted microscope at 40× magnification with Bioquant® software. Ten measurements of each dimension were taken and the average was used to determine an average cross sectional area of each sample. The overall average strip measured 1.1 cm×0.538 cm×0.080 cm.

For tensile and elongation testing, ASTM D 5035, Standard Test Method for Breaking Force and Elongation of Textile Fabrics (Strip Method), was followed with some modification due to limitations of scaffold size. Electrospun scaffolds were cut into 20 mm×10 mm strips and placed in clamps spaced 10 mm apart for a constant rate of extension (CRE) test using an Insight 5 (MTS) system with a 200 lbf load cell. Stress, strain, force, displacement and time were recorded for each strip but only stress and strain were used in analysis due to the variation in sample thickness. The test method was set up to apply a 0.5 N preload to adjust for slack in the samples then the actuator was moved at 1.000 mm/s up to 150 mm.

In an embodiment, the scaffolds may be flat. In one experiment, flat scaffolds of each parameter were cut into octagons 1.5 cm in diameter and three of each were sterilized with oxygen gas plasma while the other three were sterilized with EtO gas. Treatment occurred directly prior to seeding and samples were wetted with Smooth Muscle Growth Supplemented cell media (Medium 231+SMGS, Cascade Biologics) then incubated for 30 min. Scaffolds were seeded with Human Aortic Smooth Muscle cells (Cascade Biologics, P4) at a density of $2\times10^4$ cells/$cm^2$ using a drop seeding technique. Seeded scaffolds were placed in an incubator and media was changed every other day for 7 days. At day 7, scaffolds were fixed with 4% Formalin then stained with FITC and DAPI. Samples were analyzed using a Leica Fluorescent confocal microscope.

Based on the results from these preliminary studies on flat scaffolds, it was determined that viable mechanical properties could be achieved. In addition, our studies using hASMC support the feasibility of cells prospering on scaffolds. From this data, a more robust study featuring tubular scaffolds was designed and implemented.

In an embodiment, the scaffolds may be substantially tubular. In one experiment, tubular scaffolds were electrospun from PCL as described previously and mechanically tested using a constant rate of extension (CRE) test following ASTM D-5035 "Standard Test Method for Breaking Force and Elongation of Textile Fabrics" as a guideline, although some deviations from the method were necessary due to inherent limitations of the scaffolds. The strip method was used because it is prescribed for nonwoven textiles under the standard although it differs from some currently reported methods which use a dogbone shape. Failure was defined as the point at which the tensile strength became less than or equal to 50% of the ultimate tensile strength. A 889.64N (200 lbf) load cell sending data to Test Works 4 (MTS Systems) was used to calculate stress. Both stress and strain were recorded and graphed from the raw data recorded by Test Works 4. Nine samples of each electrospinning parameter combination were tested (n=9). However, in some cases there was slippage between the specimens and the clamps during testing and these were not included in the analysis.

A pycnometer with a 1.0 $cm^3$ chamber and helium gas (AccuPyc 1340, Micromeritics) was used to determine the true volume of each tubular scaffold, taking 10 measurements per sample. Bioquant® software was used to measure the nominal volume at 40× magnification on an inverted microscope. For the nominal measurement, samples were sandwiched between two glass slides and an area measurement was taken. Then the samples were stood on end and ten measurements of thickness were taken and averaged. The area was multiplied by the average thickness to determine an average nominal volume. The nominal volume and true volume were used to determine the porosity of the samples. Six samples from each parameter set (n=6) were measured then averaged to determine average porosity for each parameter set. Using scanning electron microscopy (SEM), images were acquired for the various parameters and evaluated for the overall morphology of both the interior and exterior of each sample.

For the degradation study, a high, medium and low porosity scaffold were chosen for analysis from scaffolds considered feasible for aortic aneurysm applications. Aorta scaffolds used with the EVAR technique are introduced into the femoral artery using a catheter. In general, smaller catheter sizes are preferred to reduce damage to the arteries. Therefore, the scaffold circumference will have to expand 5-6 times when it is deployed in the aorta. Because of this demanding high strain capacity during deployment, scaffolds with average strain values less than 550% were considered irrelevant for the degradation study. The scaffold considered to be highly porous has a porosity of 85.4±1.8%; the medium porosity scaffold is 80.9±1.5% porous; and the low porosity scaffold is 76.8±5.6% porous.

A total of 72 scaffolds were made from these three parameter sets (24 scaffolds per set) and were weighed on a microbalance then submerged in 2.0 mL Phosphate Buffered Saline (PBS) in a water bath at a temperature of 37° C. shaking at 50 RPM. After time periods of 1 hour, 30, 60 and 90 days, scaffolds (n=6) corresponding to each parameter set were removed and rinsed three times in deionized water. The scaffolds were then allowed to dry under vacuum for 48 hours at room temperature before being weighed a second time then subjected to mechanical testing as previously described. Results were compared to those of the 1 hour time point which served as control samples to determine trends in mechanical data and changes in weight loss. Care was taken to insure that samples from each time point were tested as quickly as possible and stored under vacuum with desiccant and protected from light between tests.

Parameter sets were compared using one-way ANOVA ($\alpha$=0.05) to determine significant effects of parameters on stress, strain and porosity as well as degradation. Z-test ($\alpha$=0.05) and box plots were used to determine outliers within a sample data population.

Figure 2A:
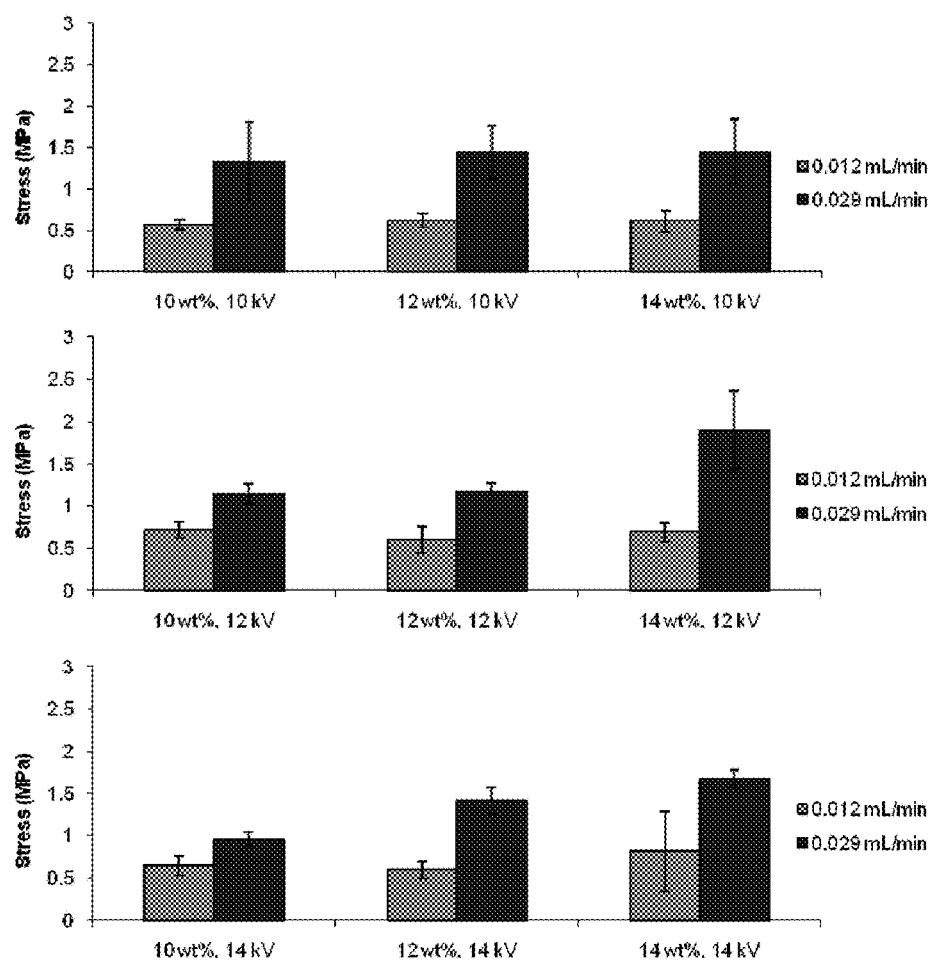
FIGS. 2A-2C depict graphs comparing the effect of solution concentration, extrusion rate and voltage on ultimate tensile stress of electrospun tubular scaffolds.
Figure 2B:
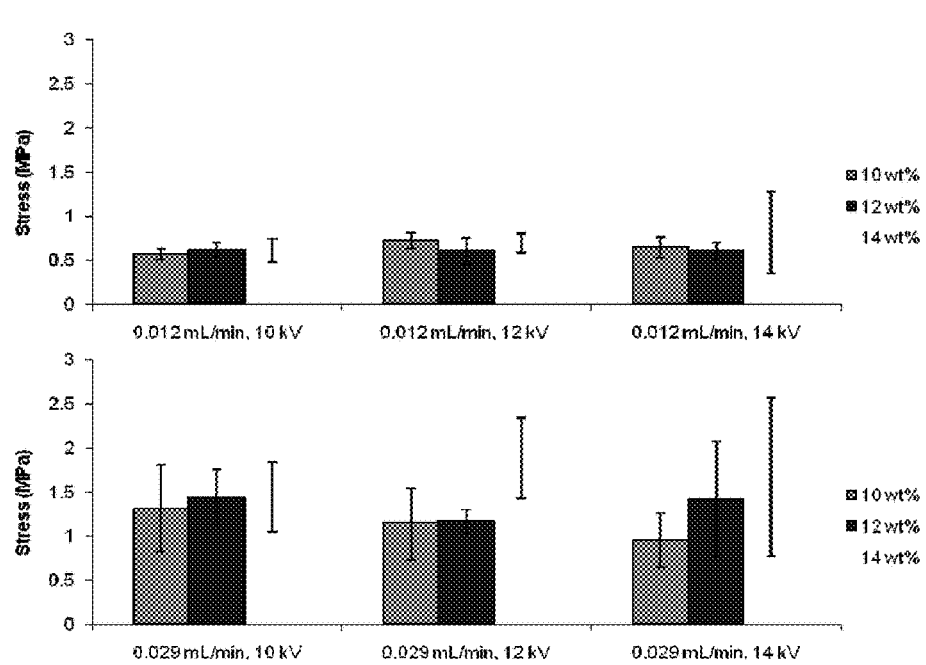
Figure 2C:
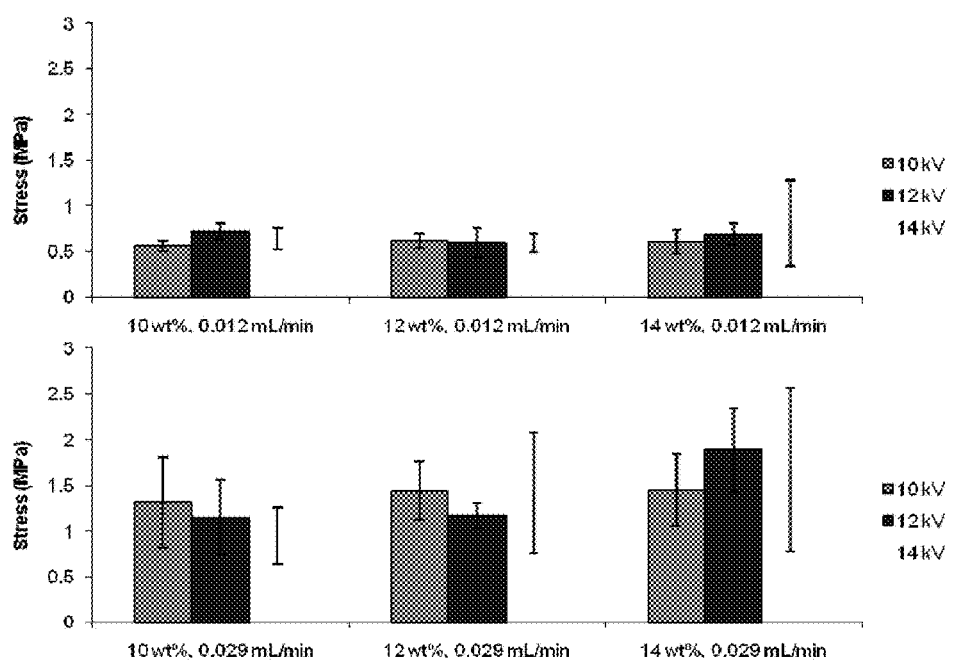

The ultimate tensile strength results from the constant rate of extension test are presented in FIG. 2. The greatest ultimate tensile strength (UTS) was 1.893±0.458 MPa.

Figure 3:
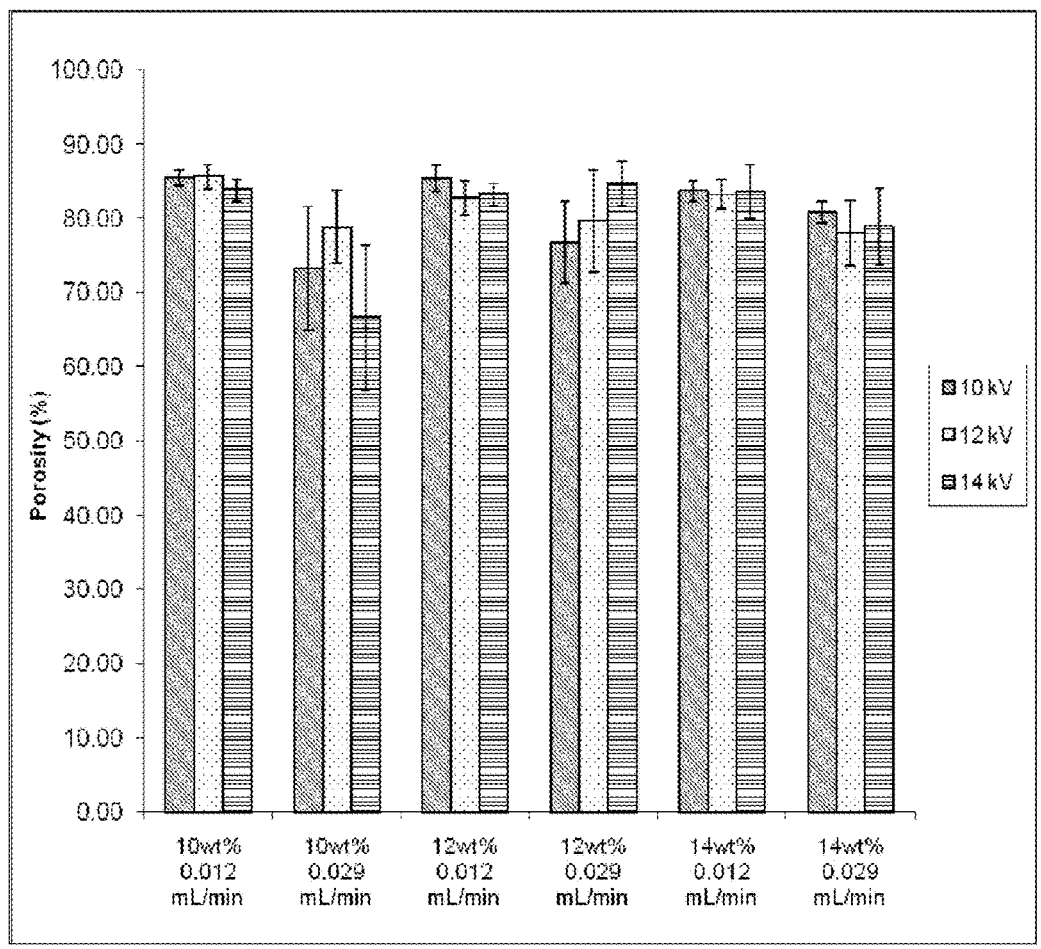
FIG. 3 depicts a graph of the average porosity of scaffolds fabricated using varying parameters.

The practical requirements for a device which is inserted in a small vessel then expanded to a large vessel include the strain which can be achieved before failure. In addition to mechanical requirements, the scaffolds are designed to be favorable for cells. This includes sufficient porosity for cell attachment, migration and proliferation. One of the touted properties of electrospun scaffolds is their fibers resembling extracellular matrix and its porous nature. The average porosity within each sample group remained, for the most part, very similar and with small standard deviations as shown in FIG. 3.

Figure 4A:
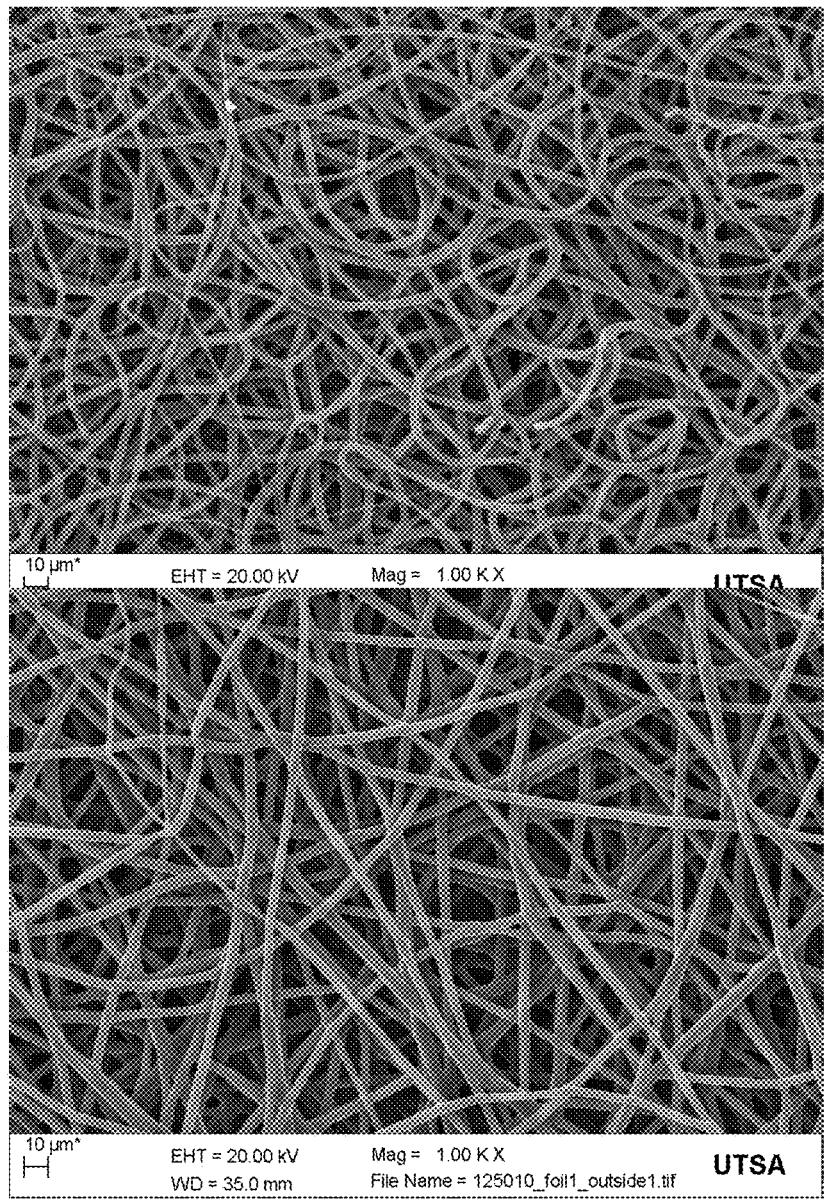
FIGS. 4A-4C depict SEM images of the contrast between the concave and convex surfaces of a single tubular scaffold representing the gradient of morphological changes throughout the scaffold.
Figure 4B:
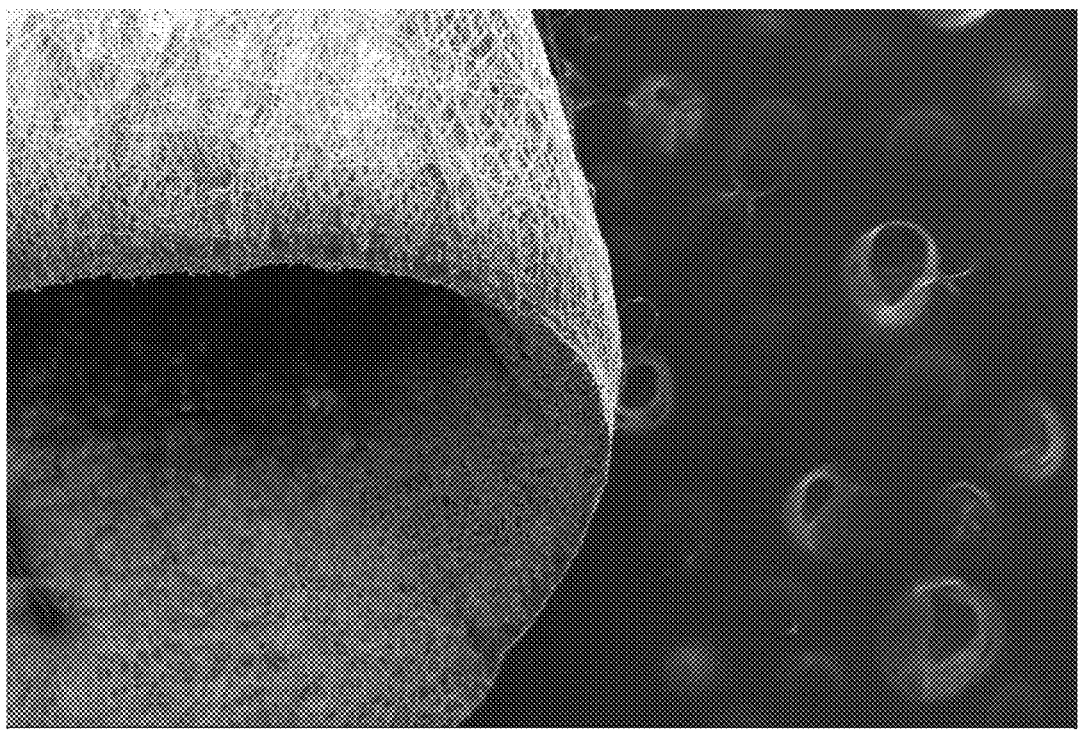
Figure 4C:
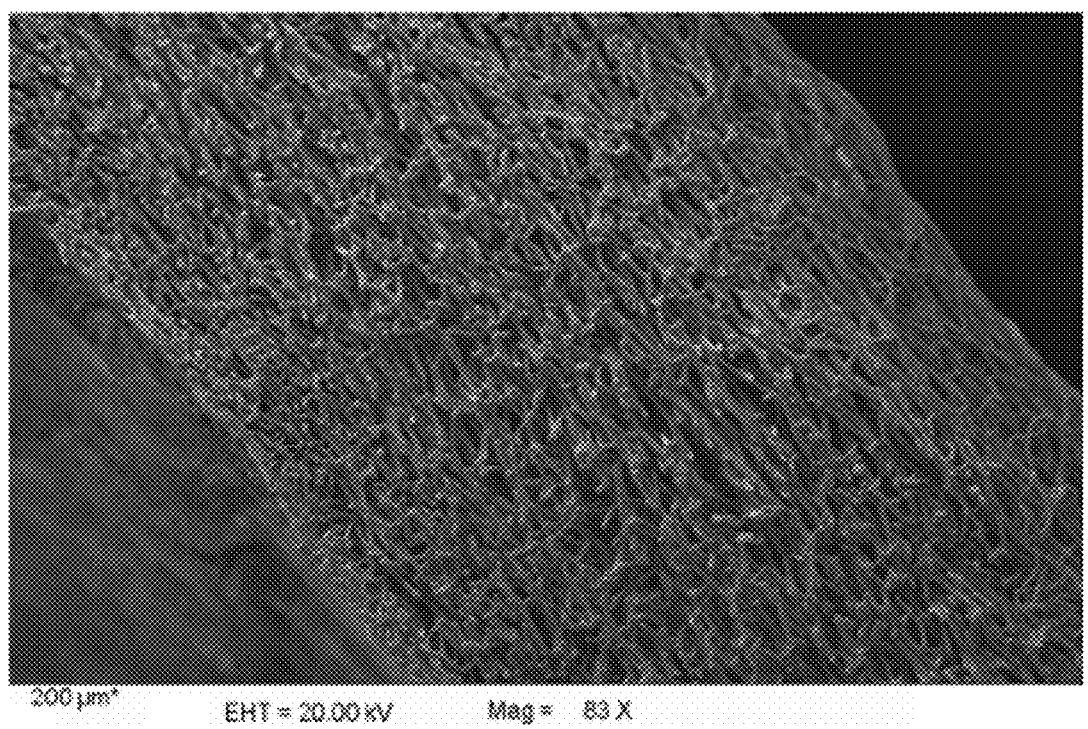

SEM images revealed mild changes in morphology from the interior of the sample to the exterior as shown in FIG. 4. The fibers on the concave side presented a more curved alignment whereas the fibers on the convex side appeared more linear.

As a bioresorbable polymer, it is expected that PCL will undergo degradation. However, it is important for the scaffolds to maintain their integrity until viable tissue is formed. It may be expected that scaffolds of higher porosity may lose integrity before scaffolds of lower porosity due to increased surface area.

Figure 5A:
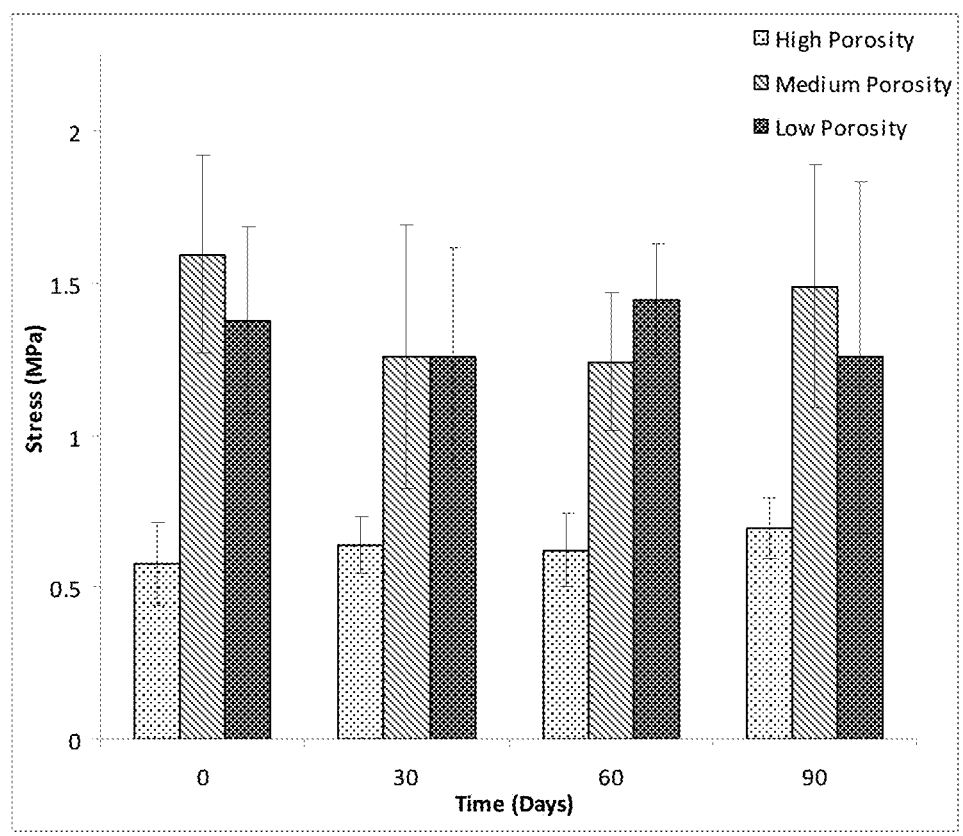
FIGS. 5A-5C depict graphs of the degradation of tubular electrospun scaffolds over 90 days in PBS at 37° C. agitated at 50 RPM (n=6)

Comparing scaffolds with different porosities over a 90 day time period, there was no significant difference between the ultimate tensile stress from one time point to the initial strength for any of the scaffolds. Results for the tensile stress over time are shown in FIG. 5A and are comparable with values obtained in other areas of this study.

Figure 5B:
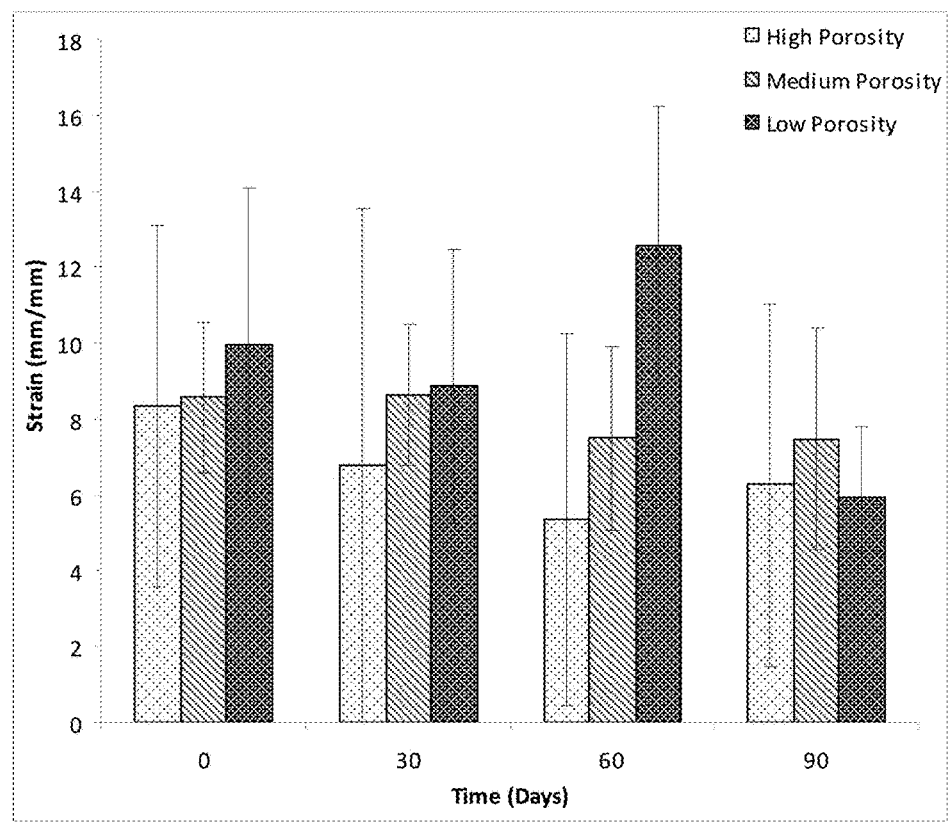

Similarly to results for UTS, there was no significant difference in strain at failure over the 90 day period for any of the scaffolds. FIG. 5B shows a graph of these results.

Figure 5C:
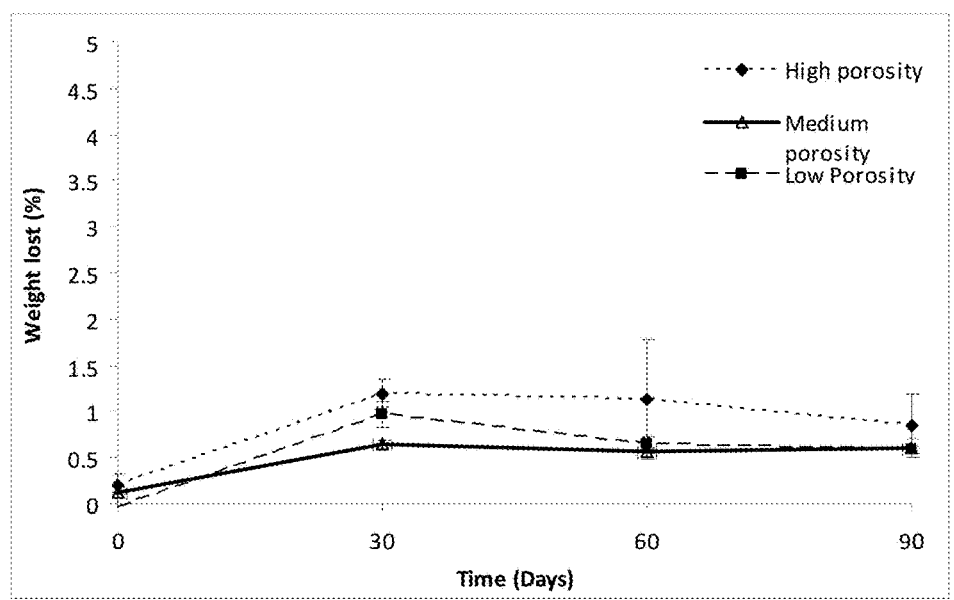

While weight loss over the 90 day time period was observed for all samples as shown in FIG. 5C, it appears to plateau after the initial loss and is minute.

The concave side having more curvilinear fibers and the convex side having more straight fibers within the same scaffold may contribute to the mechanical properties of the overall scaffold.

Figure 6:
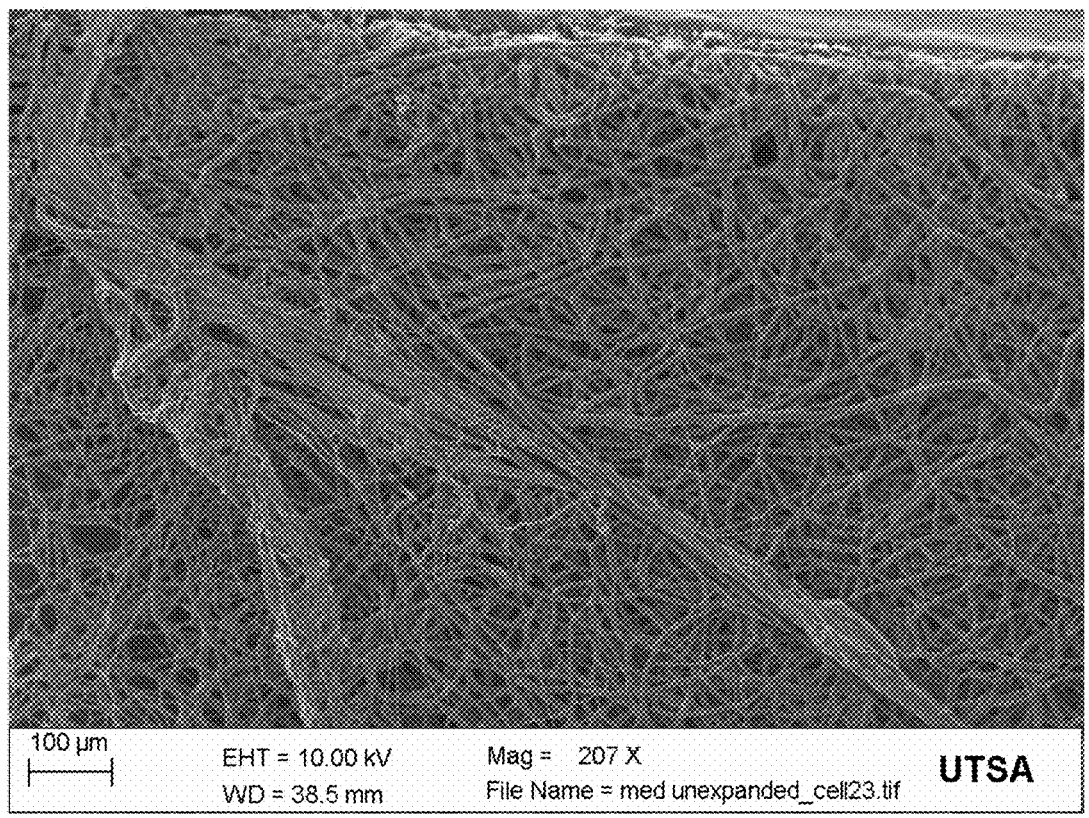
FIG. 6 depicts an SEM image of human aortic endothelial cells spread on electrospun tubular scaffold.
Figure 7:
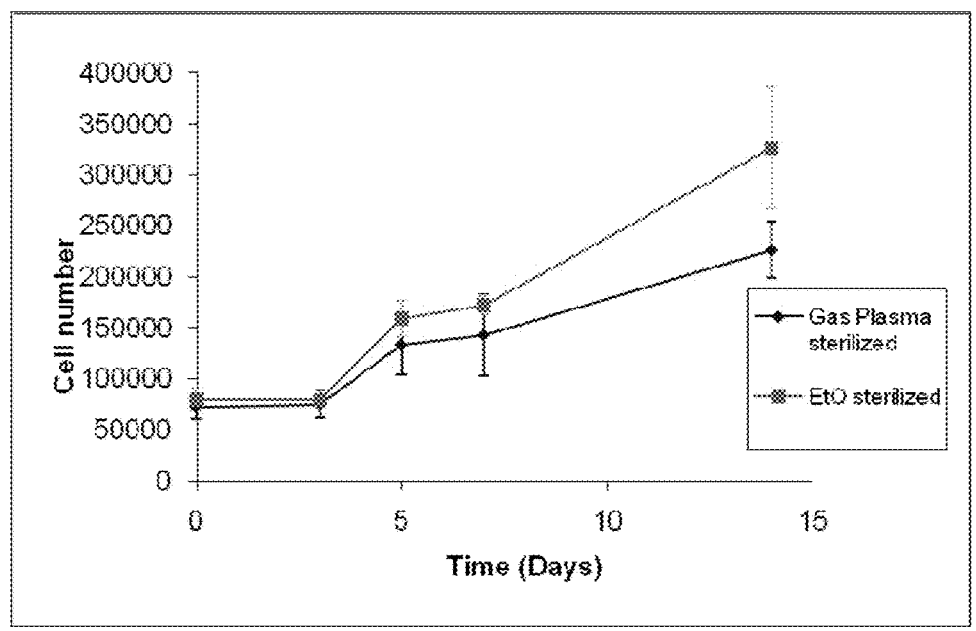
FIG. 7 depicts the metabolic activity of human aortic smooth muscle cells in static culture over 14 days on tubular electrospun PCL scaffolds.
Figure 8:
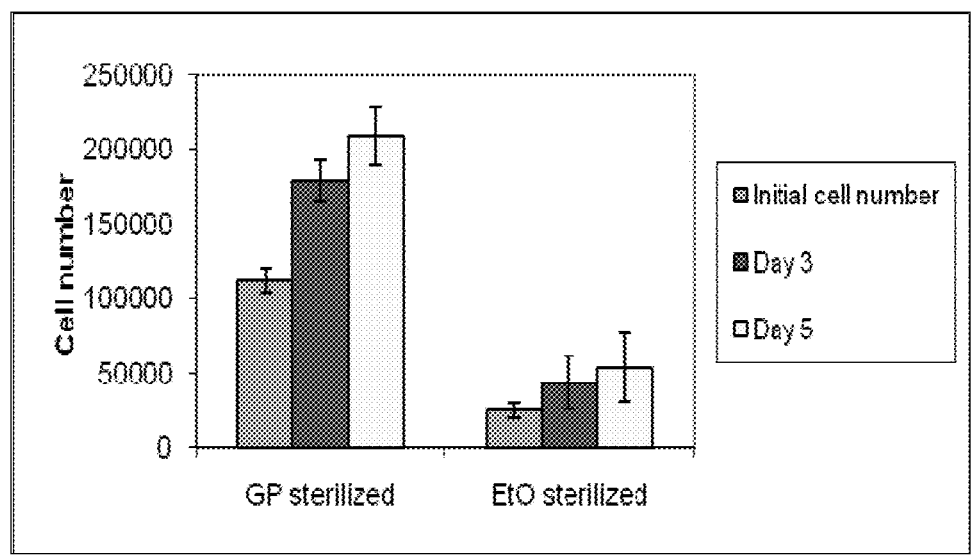
FIG. 8 depicts the metabolic activity of human aortic smooth muscle cells in a bioreactor on tubular electrospun scaffolds.

Additional studies were performed to assess cell proliferation on the scaffolds. Tubular scaffolds were placed in both static and dynamic cultures and either human aortic endothelial cells (Cascade Biologics) or human aortic smooth muscle cells (Lonza) were placed on the scaffolds to observe their respective proliferation in vitro. FIG. 6 shows human aortic endothelial cells spreading on a scaffold when cultured under dynamic flow. While studies with endothelial cells are preliminary, this spreading suggests that the endothelial cells will adhere to the scaffolds and proliferate under dynamic flow. In another study, tubular scaffolds were sterilized with either Ethylene Oxide gas (EtO) (n=3) or Oxygen Gas Plasma (GP) (n=3) then placed in individual well plates and smooth muscle cells were drop-seeded onto the scaffolds. The cells were allowed to proliferate for 14 days, with media changes every other day. The metabolic assay AlamarBlue (Invitrogen) was used to extrapolate cell number at days 0, 3, 5, 7, and 14 as shown in FIG. 7. An increase in cell number indicates that the scaffolds were conducive to cell growth and proliferation. Next, tubular scaffolds were placed in a bioreactor and exposed to a dynamic flow for 5 days with media changes every other day. Scaffolds were once again sterilized with either EtO (n=3) or GP (n=3), seeded with human aortic smooth muscle cells and AlamarBlue was used to measure metabolic activity on days 0, 3 and 5. Results from this study are shown in FIG. 8. The increase in cell number indicates that the cells can proliferate under dynamic flow. While these results are positive it is also important to note whether cells in the fluid passing by the scaffolds will attach. A study was performed in which tubular scaffolds were sterilized with either EtO (n=1) or GP (n=3) and placed in the bioreactor. However, instead of pre-seeding the scaffolds, the cells were placed in suspension in the media that would be perfusing through the system. At day 3, the scaffolds were removed and AlamarBlue was used to determine cell number. The results indicate that the cells are able to adhere to the scaffolds without pre-seeding. FIG. 9 compares the results of the suspension test to the static and dynamic tests in which the cells were pre-seeded. This is an important indication that scaffolds placed in a flow system such as the cardiovascular system will be able to retain cells in the flow thus reducing the need to pre-seed the scaffolds and in turn reducing the time a patient must wait to receive the scaffold.

Studies were conducted to compare different scaffold morphologies. PCL was prepared in three configurations. The first, "A", consisted of electrospinning a 9 wt % (e.g., about 8-10 wt %) solution of PCL in 75:25 Chloroform: Methanol (e.g., halogenated organic solvent and alcohol mixture) at 0.035 mL/min with a tip to collector distance of 15 cm and 15 kV applied to the needle of the syringe. The second, "B", used electrospinning with a 14 wt % (e.g., about 10-15 wt %) solution of PCL in Chloroform (e.g., a halogenated organic solvent) at 0.029 mL/min extrusion rate, a 10 cm tip to collector distance and 12.0 kV applied. The third set, "C", was made from casting 12 wt % (e.g., about 10-15 wt %) PCL solution in chloroform (e.g., a halogenated organic solvent) on a piece of glass, under a Styrofoam box. After the chloroform evaporated, a film was left which was consistently the same thickness as the B setup, approximately 0.5 mm. The "A" setup produced thinner scaffolds, approximately 0.3 mm. "C" samples serve as a control to compare the theoretical three-dimensional structure of "A" and "B" with a two-dimensional structure. The collector, as mentioned before, consisted of a piece of aluminum foil, shiny side up, which covered an aluminum screen with the negative terminal of the high voltage source applied. After making the scaffolds, they were cut into 5 mm×5 mm squares using a straight razor blade. SEM was used to image the scaffolds to determine average fiber diameter. FIGS. 10A-B depict SEM images of electrospun scaffolds "A" (nano) and "B" (micro) at 2000×.

In some embodiments, scaffolds were sterilized in open glass scintillation vials by exposing them to high RF oxygen gas plasma for 3 minutes. Scaffolds were grouped for sterilization so that all time points for a group for both cell types were sterilized together to reduce the error that may result in different sterilization within a group. After sterilization, samples may be exposed to sterile cell culture media for their respective cell types in individual wells of ultra-low adhesion well plates.

Human aortic endothelial cells (EC) and human aortic smooth muscle cells (SMC) were purchased from Lifeline cell technologies. The SMC donor was a 49 year old African American male, non-smoker, with hypertension and cardiac disease who died from intracerebral hemorrhage. The EC donor was a 61 year old Caucasian male, non-smoker, with hypertension and cardiac disease who died of intracerebral hemorrhage. SMC were cultured in Invitrogen's basal media, M231, with smooth muscle cell growth supplement and EC were cultured in Lifeline's basal media with Endothelial growth supplement. Both cell types were brought up through P5. Cells were trypsinized, centrifuged, resuspended and counted using a hemacytometer. SMC were introduced to wells with SMC media at a concentration of 4×10$^4$ cells/scaffold. EC were introduced to wells with EC media at a concentration of 4×10$^4$ cells/scaffold. Standard curves were also made by seeding a range of volumes of each cell type into a regular well plate. Three scaffolds for each time point were seeded and three replications for the standard curve were seeded. Cells were allowed to attach for 2.5 hours before initial analysis. For metabolic data, this study was replicated 4 times, for proliferation data, the study was replicated twice and for microscopy the study was replicated twice. An n=3 was used for each replication.

Figure 11A:
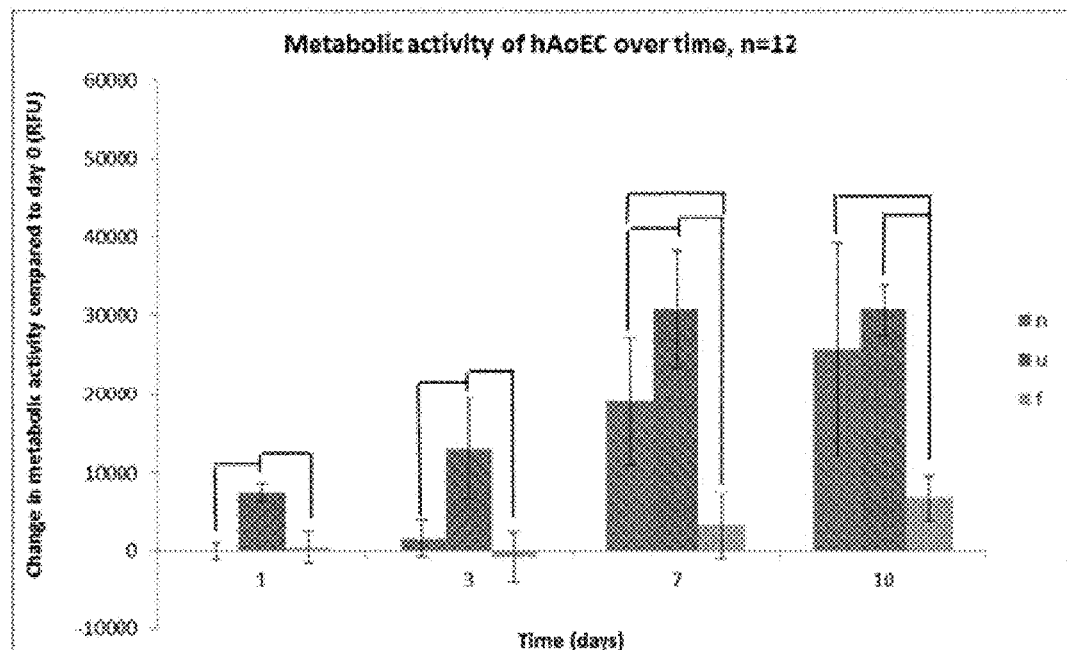
FIGS. 11A-B depict graphs of change in metabolic activity of hAoEC and hAoSMC in response to scaffolds of different fiber morphology (normalized to day 0 values for each sample)
Figure 11B:
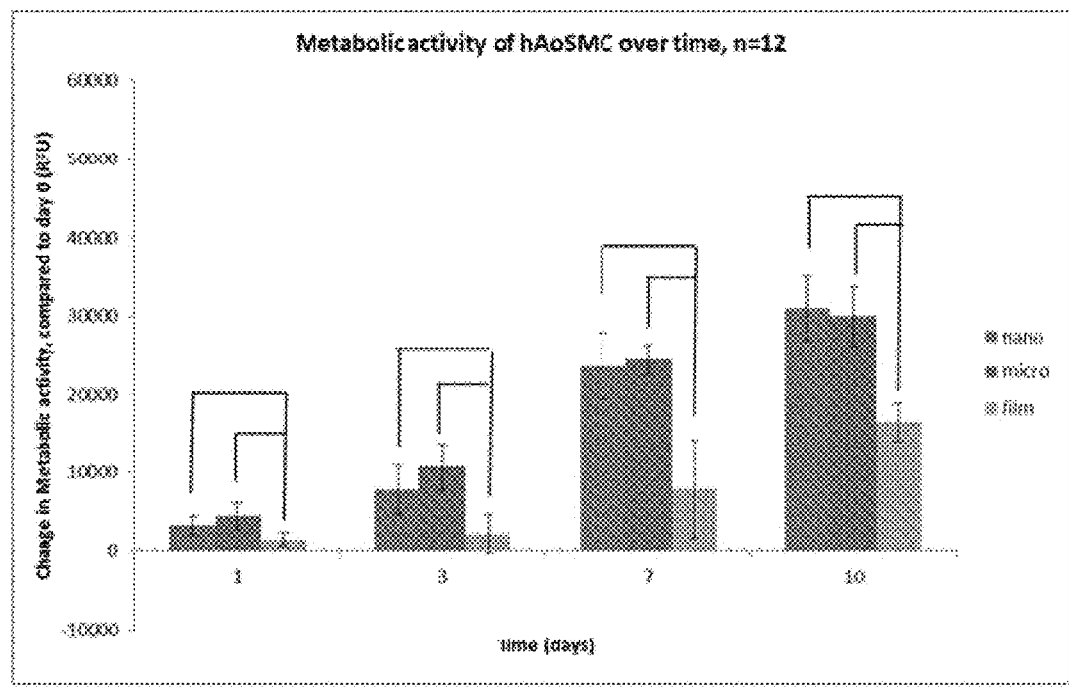

To measure metabolic activity, media was withdrawn from the scaffolds and a 10% alamarBlue (AB) solution in media was added to each well, including the standard curves. The AB solution used the respective media for each cell type. Scaffolds were incubated for 2.5 hours with the AB then the AB was aliquoted in 100 µL volumes into black opaque 96 well plates and read with a fluorescent plate reader at EX:530 EM:590. After AB solution was removed from the wells, scaffolds were rinsed with PBS then plates with day 0 time point scaffolds were wrapped in parafilm and placed in the −80 C freezer. Media was replaced in the remaining scaffolds and the plates were placed back in the incubator. This AB process was repeated for days 1, 3, 7 and 10. FIGS. 11A-B depict graphs of change in metabolic activity of hAoEC and hAoSMC in response to scaffolds of different fiber morphology (normalized to day 0 values for each sample).

Figure 12A:
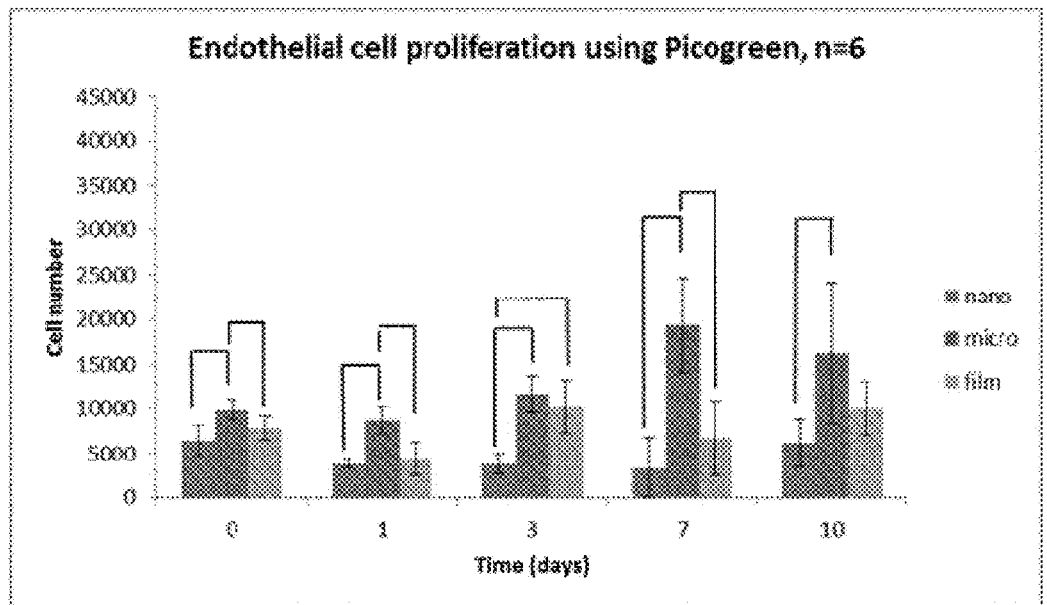
FIGS. 12A-B depict graphs of cell proliferation over time of hAoEC and hAoSMC on scaffolds composed of either nanofibers (A), microfibers (B) or films (C). Determined using Picogreen to measure dsDNA content, n=6.
Figure 12B:
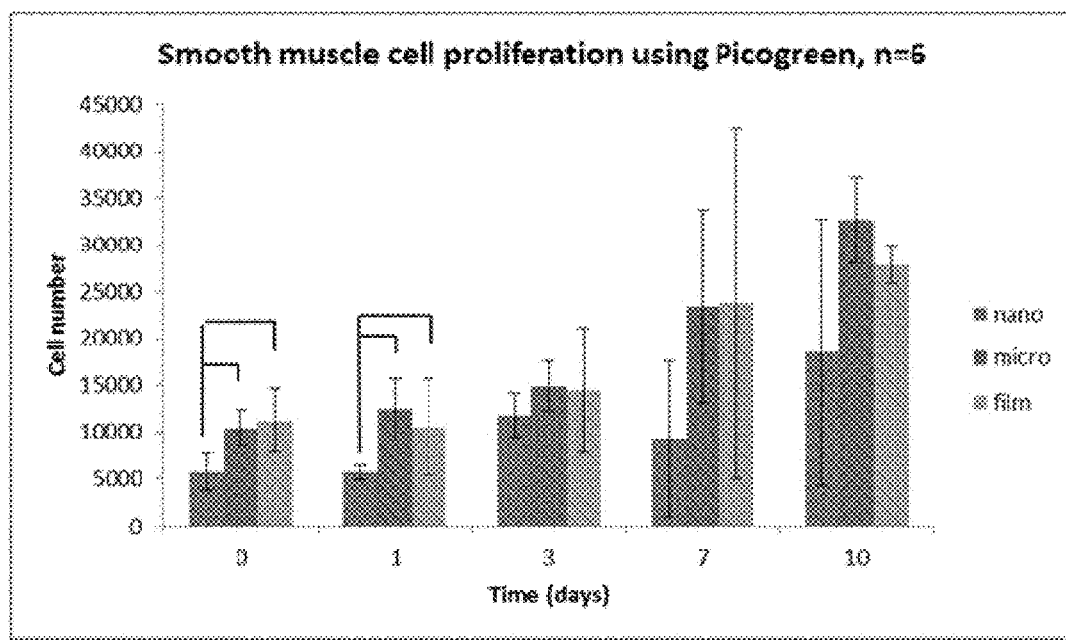

After all time points were completed and frozen, a dsDNA quantification study was performed using Picogreen (PG). Scaffolds were removed from −80° C. and allowed to thaw for 30 min at RT. Proteinase K was diluted in EC media to 1 mg/mL and 100 µL was added to each sample and standard curves. The plates were placed in the incubator which was ramped up to 42° C. for 30 min. Plates were removed and placed on a plate shaker for 2 min at #3 intensity. The plates were then placed back in −80° C. and left overnight. The next morning, the plates were removed from the −80° C. and allowed to thaw at room temperature for 30 min. They were once again placed on a plate shaker for 2 min at #3 intensity before being frozen a third time at −80° C. for another 30 min then thawed at room temperature for 30 min. 500 µL of TE buffer was added to all of the Plate 1 samples. Then 5 replicates of 100 µL each was removed to a DNAse and RNAse-free 96 well plate. Plates 2 and 3 were placed in −20° C. freezer. The PG assay solution was mixed and consisted of 100 µL PG with 21 mL of TE buffer. 100 µl of PG solution was added to the well plates so that the total volume per well was 200 µL. The plates were allowed to incubate a few minutes in the dark then read with a fluorescence plate reader at EX:485 EM:528. The same technique was repeated for plates 2 and 3. FIGS. 12A-B depict graphs of cell proliferation over time of hAoEC and hAoSMC on scaffolds composed of either nanofibers ("A"), microfibers ("B") or films ("C"). Determined using Picogreen to measure dsDNA content, n=6.

Scanning electron microscopy was used to image both fibrous scaffolds before the introduction of cells as well as at each time point. When cells were present, the samples were fixed in 4% Paraformaldehyde, then dehydrated using an ethanol gradient before being placed in a vacuum oven at room temperature.

Samples for each time point were fixed in 4% paraformaldehyde then stained with either α-actin conjugated FITC or anti-CD-31 with a fluoraphor and DAPI to stain the nuclei. The samples were mounted in Slowfade then observed with a confocal fluorescence microscope using their respective wavelengths. FIGS. 13A-D depicts SEM images of electrospun microfibers with human aortic endothelial cells on days 1, 3, 7 and 10. FIGS. 14A-D depicts SEM images of electrospun microfibers with human aortic smooth muscle cells on days 1, 3, 7 and 10.

One-way ANOVA was used to determine a significant increase in cell number and metabolic activity. Tukey test was used Post hoc. A z test was used to determine outliers.

Based on both metabolic and proliferation data, it can be determined that endothelial cells respond more positively to microfibers than either films or nanofiber scaffolds made of the same material. More specifically, it should be noted that on the nanofibers, the endothelial cells show increased metabolism but not increased proliferation suggesting that the cells may be distressed. A similar trend is observed on the film controls but not on the microfiber scaffolds. The contrast of metabolic activity as well as proliferation with visual images for microfiber scaffolds suggests that the cells have infiltrated the scaffolds, unlike the other samples.

In vivo studies were performed using a surgical AAA model in swine. To create the aneurysm in the swine, a synthetic graft or elliptical patch of smooth muscle tissue, commonly jejunum or peritoneum, is sutured into a longitudinal laceration of the aorta and bulges to create the aneurysmal shape. The patch model creates the physical shape of an aneurysm with some inherent damage to the aorta wall.

Female swine (50-75 kg) were placed on a liquid diet for 48 h then fasted for 24 h before being tranquilized with a mixture of Diazepam (0.1 mg/kg), Ketamine (10 mg/kg) and Atroprine (0.01 mg/kg) through intramuscular injection. The animals were then anesthetized with intravenous Propofol (2 mg/kg) then orally intubated. After intubation, general anesthesia was maintained with 2% Halothane. Heart rate, blood pressure, end tidal $CO_2$ and $O_2$ saturation were constantly monitored. Venous access was established for hydration and drug administration periprocedural.

Prior to the formation of the AAA, ultrasound was used to measure the aorta to achieve a baseline reference. Under sterile conditions, a midline laparotomy was made and a portion of peritoneum was removed, folded in half and fashion into a rectangle approximately 3 cm long and 2 cm wide. Ligating clips were used proximally, medially and distally to secure the edges and form a double layered patch.

The intestines were moved to the side and covered by a damp surgical towel to reduce post-operative adhesions. The aorta was isolated and clamped off below the renal arteries using atraumatic vascular clamps. An aortotomy was made 3 cm long and 2 mm wide, parallel with the length of the aorta. The patch was sutured into the incision using 5-0 Prolene running sutures. The clamps were then removed and the aneurismal bulge, was inspected for leaks.

Leaks were closed with 5-0 Prolene sutures. When no leaks were observed, the intestines were replaced and the animal was closed in 3 layers using 3-0 Vicryl and ending with staples. The animal was recovered under veterinary care using IM analgesia with Buprenorphine 0.05 mg/kg every 12 hr during the first 24 hrs. Amoxiciline (20 mg/kg/day) was administered intramuscularly for 3 days. A dose of 375 mg of aspirin was given orally once a day for 7 days. Normal diet was resumed 1 day following the procedure. The aorta at the site of the patch was measured using ultrasound at 7 and 14 days. At 14 days, if the aneurysm measured at least 30% greater than the regular aorta, the second procedure was performed. If it was not large enough, it was allowed an additional week to form.

Solutions of polycaprolactone in chloroform were electrospun onto a rotating (587.5 RPM) 3 mm diameter aluminum mandrel to form tubular scaffolds. The resulting scaffold had the following properties: 6.37±1.13 µm average diameter fibers with an average porosity of 76.79±5.60%, an elastic modulus of 1.66±0.99 MPa, UTS of 1.45±0.32 MPa, and strain at failure of 9.52±2.73. The scaffolds were removed and cut into lengths of either 30, 35 or 40 mm. Scaffolds were individually sterilized using oxygen gas plasma with high RF for 3 minutes.

Fourteen to twenty-one days after the first procedure, a second procedure was performed to treat the aneurysm endovascularly. In the second procedure, the animals were sedated using Ketamine (100 mg/ml)+Xylazine (100 mg/ml) cocktail IM at 3 cc/50 lbs or Telazol 5-8 mg/Kg, followed by intubation and maintained on 0.3%-3% isoflurane anesthesia with supplemental oxygen using an anesthesia machine for the duration of the procedure (approx. 2 hours). An IV line was introduced and a fluid drip was started and maintained throughout the surgical procedure (0.9% normal saline solution or Lactated Ringer Solution). EKG, respiration rate, $SPO_2$, and temperature were monitored throughout the surgical procedure.

Animals were divided into 4 treatment groups as shown in Table 1.

TABLE 1

|  | Group A | Group B | Group C | Group D |
| --- | --- | --- | --- | --- |
| Aneurysm | Yes | Yes | Yes | No |
| Treatment | PCL Scaffold | Commercial PTFE stent (Atrium) | No treatment | PCL Scaffold |
| Number of animals | 7 | 4 | 2 | 4 |

On the day of surgical implantation, scaffolds for Groups A and D were sutured onto stents (Megalink Biliary Stent, Guidant Corporation) using 6-0 Prolene anchor sutures. Two anchor sutures were placed proximally with 180° offset and 1 suture was placed distally. The device was then loaded onto a balloon catheter (Powerflex P3, CTA dilation catheter, Johnson and Johnson.

For all animals, the right femoral artery was isolated and an introducer sheath (7 F) was placed into the artery. A guidewire (3 mm J, 0.89 mm×145 cm, Boston Scientific) was inserted and located just proximal to the site of the aneurysm. Following the guidewire, a multipurpose catheter (6 F) was inserted and contrast solution (Omnipaque) was used to visualize the aneurysm using angiography.

Group A:

After visualization of the aneurysm, the introducer sheath was replaced with a larger sheath (11 F) and the guidewire was replaced by a 260 cm stiff wire. The catheter loaded with the scaffold was inserted through the sheath and positioned such that the scaffold was just proximal to the origin of the aneurysm. The balloon was then expanded to 12 ATM for 10 seconds before being deflated. The stent was checked for full expansion using angiography before the balloon was removed. If it was not fully expanded, the balloon was re-expanded for an additional 10 seconds to 12 ATM. After the balloon was removed the multipurpose catheter was once again inserted and contrast solution (Omnipaque) was used to visualize the aorta and observe the degree of aneurysm occlusion. The catheter was then removed followed by the introducer sheath as the femoral artery was ligated using silk suture material. The access site was closed with 3-0 Vicryl and the animal was recovered.

Group B

For the second group of animals, the PTFE covered stent (Atrium I-cast, 9 mm) which was preloaded on a balloon catheter was inserted through the 7 F introducer sheath following the guidewire to the site of the aneurysm. The balloon was expanded to 15 ATM for 10 seconds then deflated and removed. The $2^{nd}$ balloon (Powerflex P3 CTA catheter 12 mm×4 mm) was then placed and inflated to 12 ATM for 10 seconds proximal and distal. The 6 F MP-1 catheter was re-placed and angiography was used to determine if the AAA was properly occluded. The guidewire and catheter were then removed, followed by the sheath as the femoral artery was ligated with silk. The access site was closed using 3-0 Vicryl and the animal was recovered.

Group C

For the control Group C, the bare balloon (Powerflex P3 CTA catheter, 12 mm×4 mm), (without anything loaded) was inserted through the 7 F sheath and expanded to 12 ATM for 10 seconds. It was then removed and the 6 F MP-1 catheter was used to visualize the aorta with angiography.

After the catheter and sheath were removed, the femoral artery was ligated with silk and the animal was recovered.

Group D

Animals in group D did not undergo an aneurysm surgery but did receive a scaffold as described for Group A.

Ultrasound was used to determine the size of the aorta before the initial surgery as well as at 7, 14 and in select cases 21 days after the aneurysm formation. Twenty-one days were allowed if the aneurysm size was not at least 30% greater than the native aorta at 14 days. After the second procedure, ultrasound was used to examine the aneurysm at 14 and 28 days post op. For all ultrasounds, the animal was under sedation (Telezol 5-8 mg/Kg IM) and the aorta at the site of the aneurysm was measured at three points from three images at each time point.

In addition to the ultrasounds, angiography was used during the second procedure and at the sacrifice to gain both straight and lateral images of the aorta. Three aneurysm measurements were taken from angiography images of each animal.

After 28 days, the animals were placed under general anesthesia and the left femoral artery was isolated. A 6 F introducer sheath was placed and a 6 F HS catheter was placed. Contrast (Omnipaque) was used with angiography to visualize the graft site then the animal was euthanized and a necropsy was performed. During the necropsy, the aorta was separated from the renal arteries to the iliac bifurcation. The tissue specimens were cut longitudinally to expose the lumen and gross images were obtained before fixing the specimens in formaldehyde. Once the tissues were fixed, three blocks were cut for histology: 1) Transverse through the aneurysm; 2) Longitudinal through the proximal site of apposition; 3) Transverse proximal to the aneurysmal site. The blocks were embedded in paraffin and sectioned for staining. Histological sections were stained with either Hematoxylin and Eosin (H&E), Masson's Trichrome (TRI), or immunological stains for Smooth Muscle Actin (SMA) or PECAM-1 (CD31). The H&E stain revealed overall structure of the tissue in which red blood cells are red, nuclei are blue, and cytoplasm and extracellular matrix are pink. To further elucidate the structure, TRI stained collagen blue, nuclei black, muscle red and cytoplasm pink was used. The SMA antibody was used to stain alpha-actin red. CD31 antibody stains a glycoprotein in endothelial cells and platelets brown in the sections. Immunological sections were counterstained to show the nuclei in blue. Stained slides were viewed with a light microscope. The Kruskal-Wallis analysis of ranks was used to determine a significant decrease in aneurysm size after graft implantation.

One animal each from Groups A and B died early in the study from gastrointestinal complications 1 week after the initial aneurysm formation surgery. Diet was determined to be the most likely contributor. It was adjusted for subsequent animals with no further complications noted. One additional animal from Group A died of pulmonary edema 6 hours after the placement of the graft. It was determined by the veterinary pathologist on staff that the complications were not related to the graft itself. All other animals survived the length of the study with no complications.

Figure 15:
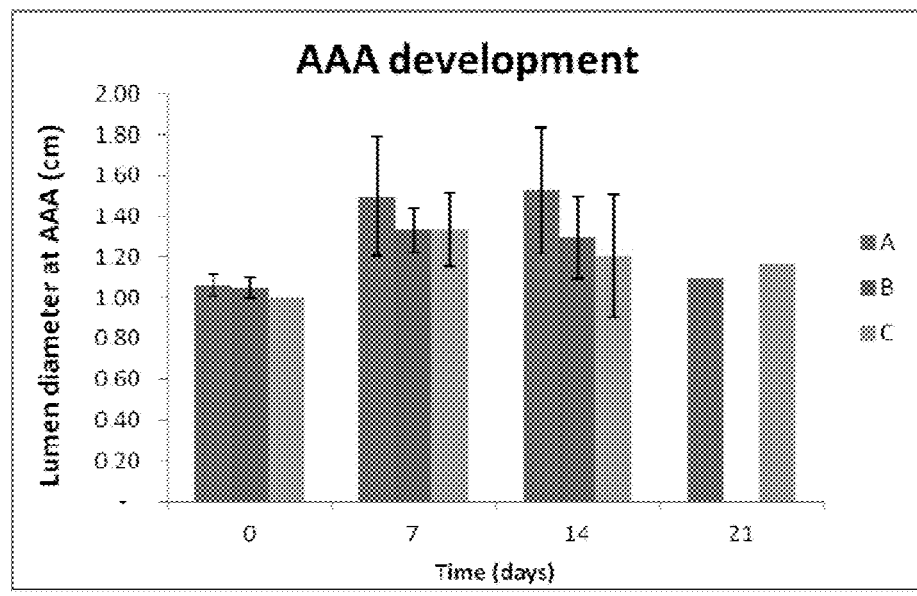
FIG. 15 is a graphical depiction of Aorta size at the aneurysm site during a period of aneurysm formation.
Figure 16A:
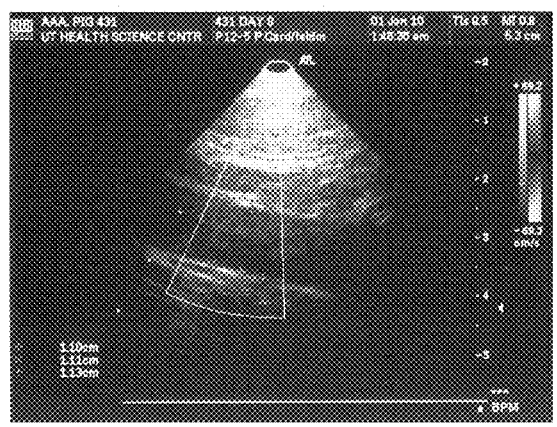
FIGS. 16A-C depicts ultrasound images of a swine aorta before surgery, 7 days after surgery and 14 days after surgery.
Figure 16B:
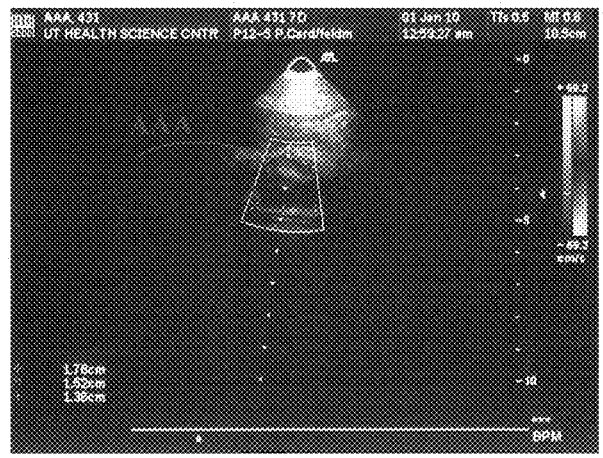
Figure 16C:
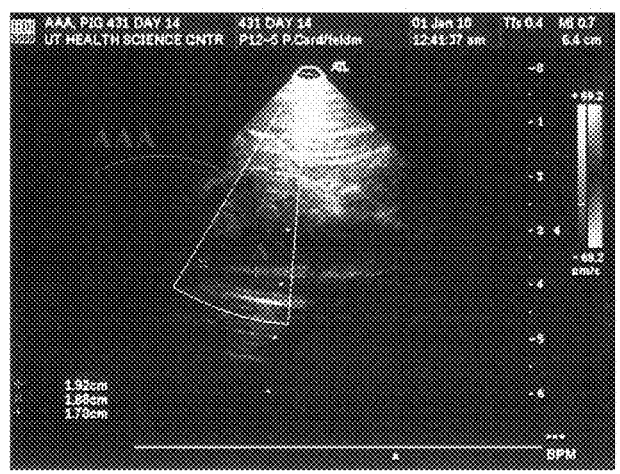

Aortic distension from the patch occurred in all of the animals that underwent aneurysm formation surgeries. FIG. 15 is a graphical depiction of the size of the initial aorta for each group compared to the average maximum lumen diameter at the site of the patch over time measured using ultrasound as shown in FIGS. 16A-C, where A is aorta and AAA is aneurysm. FIG. 16A depicts an ultrasound of the aorta before aneurysm formation surgery. FIG. 16B depicts an ultrasound of the aorta in FIG. 16A 7 days after surgery. FIG. 16C depicts an ultrasound of the aorta in FIG. 16A, 14 days after surgery.

Figure 17A:
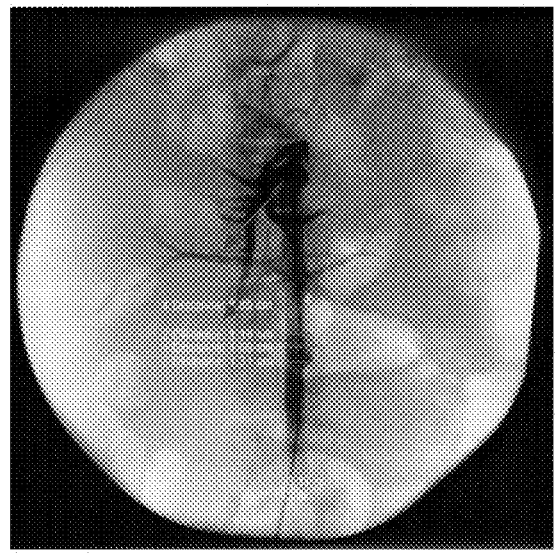
FIG. 17A depicts an angiograph of an abdominal aorta with aneurysm before treatment.
Figure 17B:
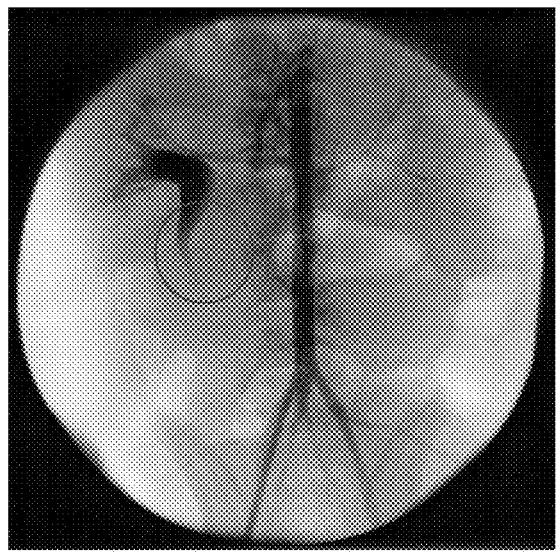
FIG. 17B depicts an angiograph of an abdominal aorta aneurysm occluded by scaffold graft.
Figure 18A:
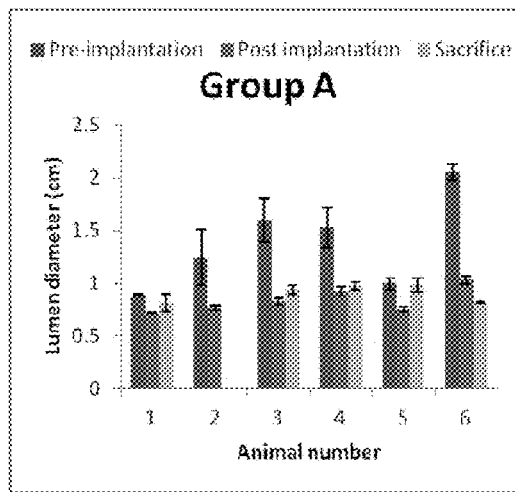
FIGS. 18A-D depict graphs of lumen diameter of individual swine using angiography before and after implantation as well as at the end of the trial
Figure 18B:
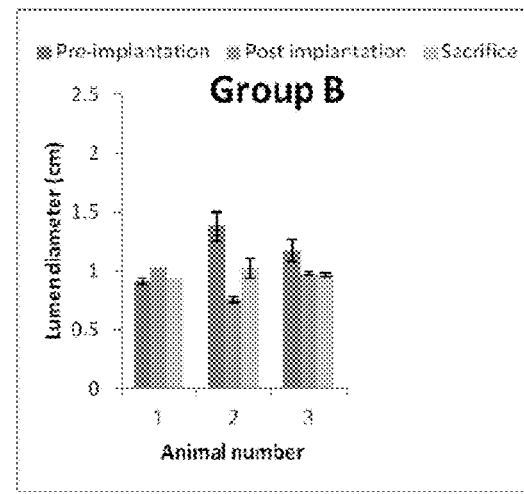
Figure 18C:
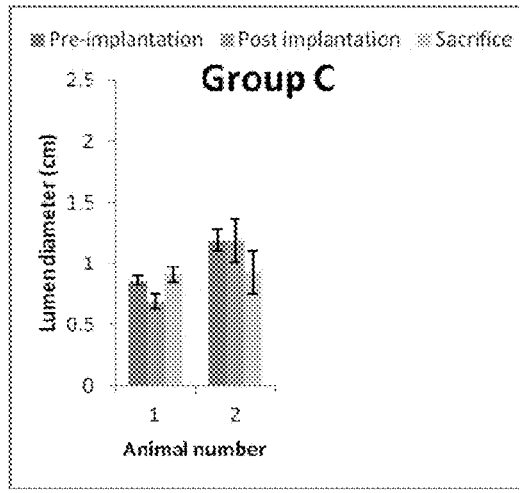
Figure 18D:
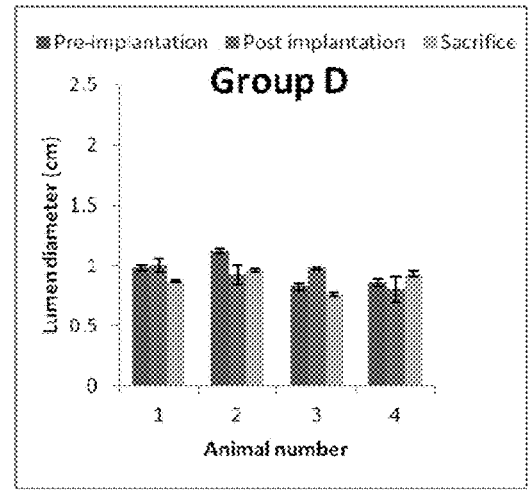

In addition to ultrasound, angiography was used periprocedural to assess the aneurysm occlusion as shown in FIG. 17A-B as well as to estimate the size of the aorta at the aneurysm level as shown in FIGS. 18A-D for the individual animals. FIG. 18A is the lumen diameter of individual animals in Group A. FIG. 18B is the lumen diameter of individual animals in Group B. FIG. 18C is the lumen diameter of individual animals in Group C. FIG. 18D is the lumen diameter of individual animals in Group D.

Figure 19A:
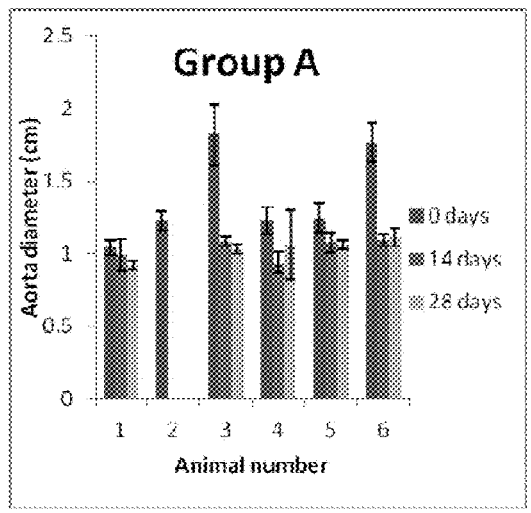
FIGS. 19A-D depict graphs of aorta size of individual swine using ultrasound at 0, 14 and 28 days.
Figure 19B:
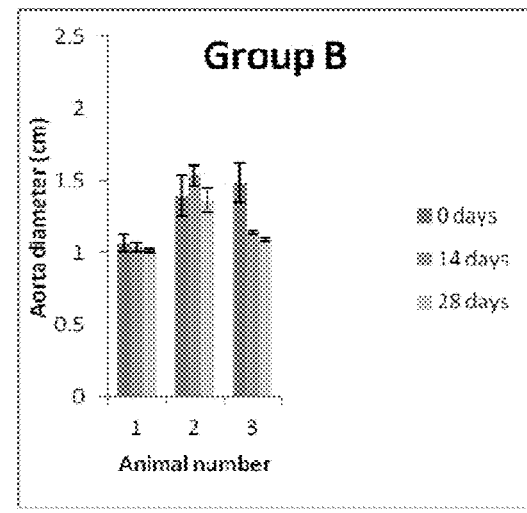
Figure 19C:
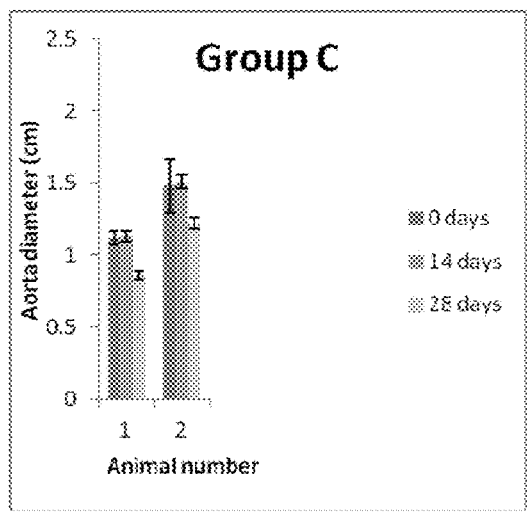
Figure 19D:
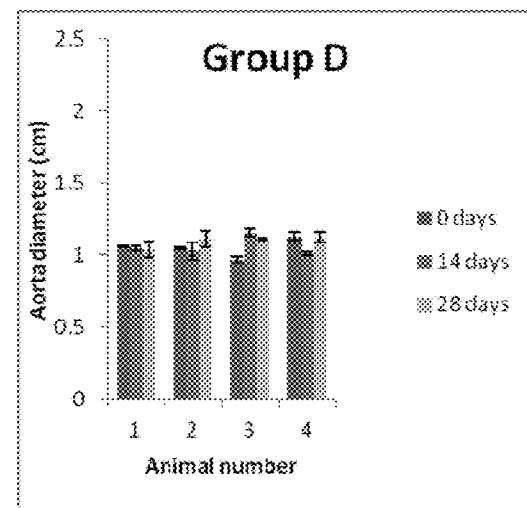

All animals were noted to have occluded aneurysms and the grafts at the aneurysm site before the procedure was considered complete. The individual results in FIGS. 18A-B show that in groups which had a graft placed over an aneurysm (groups A and B), the lumen diameter was less after implantation with the exception of the first animal in Group B which was minute and may be attributed to over distension of the balloon. The lumen diameter of animals which did not receive a graft (group C) or received a graft but there was not an initial aneurysm surgery (Group D) remained relatively consistent. After the aneurysm was treated, ultrasound was used at 14 and 28 days to determine the size of the aorta at the aneurysm site as shown in FIGS. 19A-D. FIG. 19A is the lumen diameter of individual animals in Group A. FIG. 19B is the lumen diameter of individual animals in Group B. FIG. 19C is the lumen diameter of individual animals in Group C. FIG. 19D is the lumen diameter of individual animals in Group D.

When aortas from groups A and D were opened longitudinally, it was noted that the scaffold was adherent to the aorta wall. Group A scaffolds had a change in coloring in a circular shape where the aneurysm was covered but generally appeared whitish and shiny. Aortas from group B had a red or purplish color and were somewhat shiny. Group C aortas had a slight recess where the aneurysm was and they were white and shiny, similar to the regular lumen. In group D, the lumen also appeared shiny and with no thrombosis.

Figure 20:
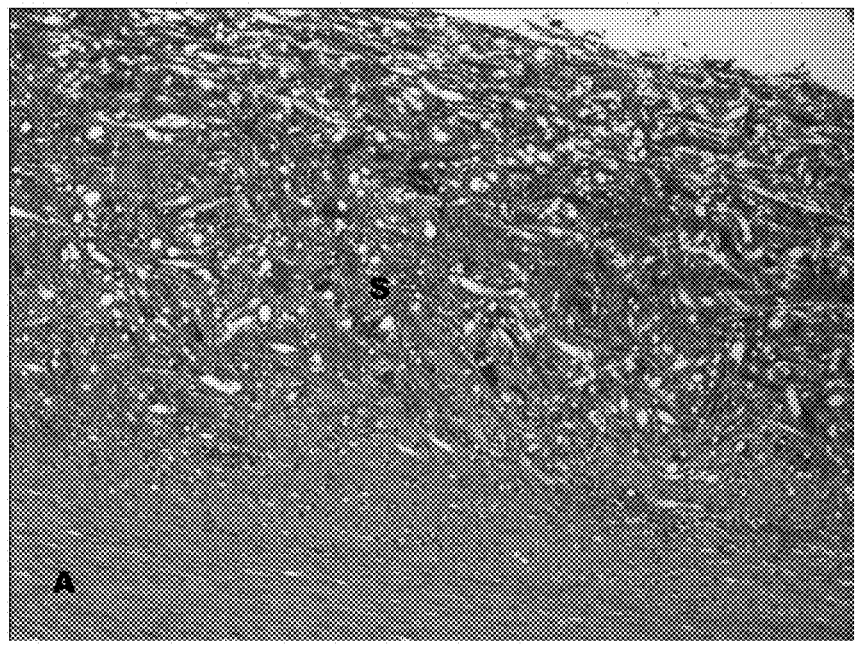
FIG. 20 depicts an H&E stain of the interface between the aorta wall (A) and scaffold (S)
Figure 21:
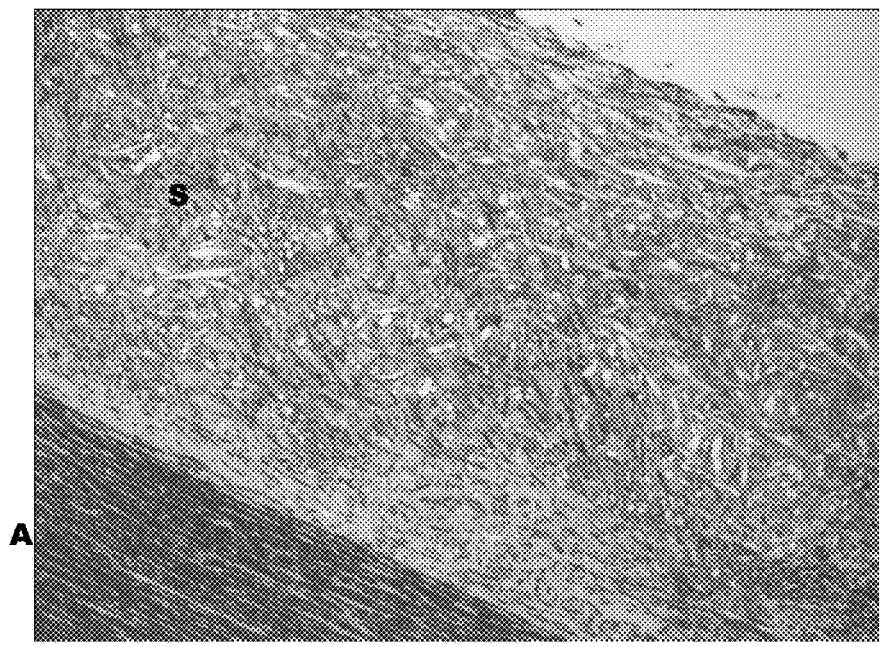
FIG. 21 depicts an smooth muscle actin stain between the aorta wall (A) and scaffold (S).
Figure 22:
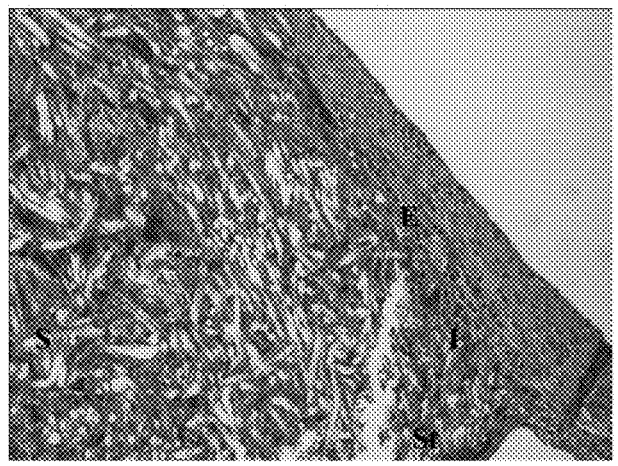
FIG. 22 depicts an H&E stain of endothelium and neointima in the aorta with a PCL scaffold implant.
Figure 23:
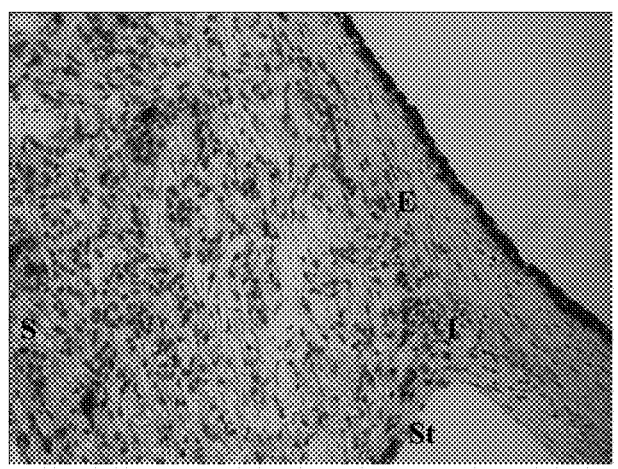
FIG. 23 depicts an CD-31 antibody stain of endothelium and neointima in the aorta with a PCL scaffold implant.
Figure 24:
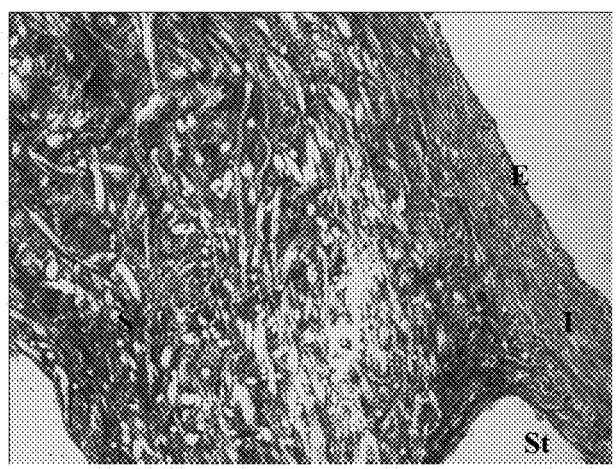
FIG. 24 depicts an Masson's trichrome stain of endothelium and neointima in the aorta with a PCL scaffold implant.

Histology results indicated that the animals in groups A and D which received the PCL scaffold had significant cell infiltration into the scaffold, as shown in FIGS. 20 and 21, including smooth muscle cell infiltration from the aorta wall. FIG. 20 depicts an H&E stain of the interface between the aorta wall (A) and scaffold (S). FIG. 21 depicts an smooth muscle actin stain between the aorta wall (A) and scaffold (S). In addition, collagen was present around the scaffold fibers. Endothelium was observed for all animals that received a PCL scaffold, demonstrated in FIGS. 22, 23 and 24 by positive staining for PECAM-1 with nuclei, where E is endothelium, S is scaffold, I in intima; and ST is removed stent strut. FIG. 22 depicts an H&E stain of endothelium and neointima in the aorta with a PCL scaffold implant. FIG. 23 depicts an CD-31 antibody stain of endothelium and neointima in the aorta with a PCL scaffold implant. FIG. 24 depicts an Masson's trichrome stain of endothelium and neointima in the aorta with a PCL scaffold implant.

There was also a neointima present between the endothelium and the scaffold consisting of collagen and smooth muscle cells oriented concentrically.

In some animals, tissue sometimes oriented perpendicular to the vessel wall appears to be separating the PTFE layers. In other portions, there was not a distinct tissue layer separating the layers suggesting that the PTFE material was intended to be presented as a single layer.

In Group C, which did not receive any treatment, the aneurysm sac filled in with what appears to be intimal hyperplasia. Therefore, it is not clearly discernible the effect of the grafts on the aneurysm itself. Such formation may be attributed to the aneurysm size, the health of the vessels, or an intrinsic response of the vascular system in swine. There were only 2 animals completed in Group C the summaries that can be drawn from the group is limited.

In the present study, endothelium and neointima was present on the scaffold and smooth muscle cells were observed within the graft material at 28 days. The PTFE covered stent showed a degree of delamination between the layers which coincided with the area of the aneurysm. Cells, sometimes oriented perpendicular to the vessel wall, bridged the gap between the layers, but did not demonstrate a viable tissue based on the lack of structural components such as collagen or smooth muscle cells in the area. There were, however, a number of neutrophils, platelets and red blood cells as demonstrated by the histological analysis. The presence of these components may be due to inflammation or indicate that the infiltration and organized tissue is slower than the response in the scaffold. The scaffold was successfully deployed in swine and demonstrated positive results for endothelialization, smooth muscle cell infiltration, collagen, and attachment to the vessel wall at 28 days.

Infiltration of the cells into the scaffold was observed both in vitro and in vivo. In vitro analysis in static conditions revealed that smooth muscle cells infiltrated scaffolds with micrometer-sized fibers more than nanometer-sized fibers. In particular, endothelial cells and smooth muscle cells demonstrated increased proliferation and metabolic activity with microfibers compared to nanofibers.

The in vitro models revealed that the cells, especially smooth muscle cells, infiltrated the microfiber scaffolds more than the nanofiber scaffolds. With testing in a dynamic environment, it was interesting to note that over time, the cells were no longer present at the endoluminal surface where many of them were initially located. In vivo, a number of cells and structural components were found within the scaffold including smooth muscle cells, collagen, and neutrophils. The endoluminal surface of the scaffold was covered by a neointima including an endothelium.

In all animals, the scaffold demonstrated a complete apposition to the aorta wall and it fully occluded the aneurysm when present. There were no significant instances of dilation or restenosis observed and the graft did not rupture despite its expansion from 3 mm inner diameter to 10 mm. Thus, the fiber type was supportive of the appropriate vascular cells and allowed for the infiltration and proliferation of these cells.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A vascular tissue repair device, comprising:
a generally tubular intraluminal scaffold having a luminal surface, an abluminal surface, and a wall thickness between the luminal surface and the abluminal surface, the intraluminal scaffold being composed of nonwoven fibers made of a biodegradable and/or bioresorbable material, the luminal surface being comprised of substantially curvilinear nonwoven fibers and the abluminal surface comprising substantially linear fibers and the abluminal surface being adapted to face and be in apposition to a luminal wall of the vascular tissue;
wherein the nonwoven fibers in the wall thickness between the abluminal surface and luminal surface exhibit a transition gradient between substantially curvilinear and substantially linear throughout the wall thickness; and
wherein the generally tubular intraluminal scaffold has an average porosity capable of cellular permeability.

2. The vascular tissue repair device according to claim 1, wherein the nonwoven fibers are made of poly(a-hyrdoxy esters).

3. The vascular tissue repair device according to claim 1, wherein the nonwoven fibers are made of polycaprolactone.

4. The vascular tissue repair device according to claim 1, wherein the generally tubular intraluminal scaffold further comprises elastin, collagen, DNA, RNA, glucosaminoglycans, polyhydroxyalkanoates or mixtures thereof.

5. The vascular tissue repair device according to claim 1, further comprising a stent.

6. The vascular tissue repair device according to claim 5, wherein the stent and the generally tubular intraluminal scaffold are diametrically expandable into apposition with the luminal wall of the vascular tissue.

7. The vascular tissue repair device according to claim 1, wherein the nonwoven fibers are electrospun fibers.

8. The vascular tissue repair device according to claim 1, wherein the nonwoven fibers are electrospun fibers and the stent is incorporated into the electrospun fibers.

9. The vascular tissue repair device according to claim 1, wherein the nonwoven fibers are treated with chemical agents, therapeutic agents or with gas plasma.

* * * * *